United States Patent [19]
Imperiali et al.

[11] Patent Number: 5,928,955
[45] Date of Patent: Jul. 27, 1999

[54] PEPTIDYL FLUORESCENT CHEMOSENSOR FOR DIVALENT ZINC

[75] Inventors: Barbara Imperiali; Grant K. Walkup, both of Pasadena, Calif.

[73] Assignee: California Institute of Technology, Pasadena, Calif.

[21] Appl. No.: 08/620,151

[22] Filed: Mar. 22, 1996

[51] Int. Cl.⁶ .................................................. G01N 33/20
[52] U.S. Cl. .......................... 436/81; 436/172; 422/82.08
[58] Field of Search ................................ 436/81, 86, 166, 436/172, 177; 422/82.08

[56] References Cited

U.S. PATENT DOCUMENTS

| | | | |
|---|---|---|---|
| 5,459,040 | 10/1995 | Hammock et al. | 436/81 |
| 5,622,821 | 4/1997 | Selvin et al. | 436/81 |
| 5,648,270 | 7/1997 | Kuhn et al. | 436/81 |

OTHER PUBLICATIONS

Minta, A.; Tsien, R.Y. "Fluorescent Indicators for Cytosolic Sodium," *J. Biol. Chem.* 1989, 264, 19449.
Tsien, R.Y. "New Calcium Indicators and Buffers with High Selectivity against Magnesium and Protons: Design, Synthesis, and Properties of Prototype Structures," *Biochemistry* 1980, 19, 2396.
Grynkiewicz, G; Poenie, M.; Tsien, R.Y. "A New Generation of $Ca^{2+}$ Indicators with Greatly Improved Fluorescence Properties," *J. Biol. Chem.* 1985, 260, 3440.
Raju, B.; Murphy, E.; Levy, L. A., et al. "A fluorescent indicator for measuring cytosolic free magnesium," *Am. J. Physiol.* 1989, 256, C540.
Bassnett, S.; Reinisch, L.; Beebe, D. C. "Intracellular pH measurement using single excitation–dual emission fluorescence ration" *Am. J. Physiol.* 1990, 258, C171.
Rink, T. J.; Tsien, R. Y.; Pozzan, T. "Cytoplasmic pH and Free $Mg^{2+}$ in Lymphocytes" *Cell Biol.* 1982, 95, 1989.
Czarnik, A. W. "Supramolecular Chemistry, Fluorescence, and Sensing" ACS, Washington D.C., 1993, p. 1.
Giuliano, K. A.; Post, P. L.; Hahn, K.M., et al. "Fluorescent Protein Biosensors: Measurement of Molecular Dynamics in Living Cells" *Ann. Rev. Biophys. Biomol. Struct.* 1995, 24, 405.
Thompson, R.B. "Enzyme–Based Fiber Optic Zinc Biosensor" *Anal. Chem.* 1993, 65, 730.
Thompson, R.B.; Patchan, M.W. "Lifetime–Based Fluorescence Energy Transfer Biosensing of Zinc," *Anal. Biochem.* 1995, 227, 123.
Virta, M.; Lampinen, J.; Karp, M. "A Luminsecence–based Mercury Biosensor," *Anal. Chem.* 1995, 67, 667.
Thompson, R.B.; Ge, Z.; Patchan, M., et al. "Fiber optic biosensor for Co(II) and Cu(II) based on fluorescence energy transfer with an enzyme transducer," *Biosensors & Bioelectronics* 1996, 11, 557.
Adams, S.R.; Harootunian, A. T.; Buechler, Y. J., et al. "Fluorescence ratio imaging of cyclic AMP in single cells," *Nature* 1991, 694.

Czarnik, A. W. "Desperately seeking sensors," *Chem. Bio.* 1995, 2, 423.
Cheng, R. P.; Fisher, S. L.; Imperiali, B. "Metallopeptide Design: Tuning the Metal Cation Affinities with Unnatural Amino Acids and Peptide Secondary Structure," *J. Am. Chem. Soc.* 1996, 118, 11349.
Torrado, A.; Imperiali, B. "New Synthetic Amino Acids for the Deisgn and Synthesis of Peptide–Based Metal Ion Sensors," *J. Org. Chem.* 1996, 61, 8940.
Walkup, G. K.; Imperiali, B. "Design and Evaluation of a Peptidyl Fluorescent Chemosensor for Divalent Zinc," *J. Chem. Chem. Soc.* 1996, 118, 3053.
Berg, J.M.; Merkle, D.L. "On the Metal Ion Specificity of 'Zinc Finger' Proteins," *J. Am. Chem. Soc.* 1989, 111, 3759.
Krizek, B. A.; Merkle, D. L.; Berg, J. M. "Ligand Variation and Metal Ion Binding Specificity in Zinc Finger Peptides," *Inorg. Chem.* 1993, 32, 937.
Krizek, B.A; Berg, J. M. "Complexes of Zinc Finger Peptides $Ni^{2+}$ and $Fe^{2+}$," *Inorg. Chem.* 1992, 31, 2984.
Berg, J. M. "Zinc Finger Domains: From Predictions to Design," *Acc. Chem. Res.* 1995, 28, 14.
Klug, A.; Schwabe, J. W. R. "Protein Motifs 5: Zinc Fingers," *FASEB J.* 1995, 9, 597.
Eis, P.S.; Lakowicz, J. R. "Time–Resolved Energy Transfer Measurements of Donor–Acceptor Distance Distributions and Intramolecular Flexibility of CCHH Zinc Finger Peptide," *Biochemistry* 1993, 32, 7981.
Frankel, A.D.; Berg, J. M.; Pabo, C. O. "Metal–dependent folding of a single zinc finger from transcription factor IIIA," *Proc. Natl. Acad. Sci. U.S.A.* 1987, 84, 4841.
Godwin, H. A.; Berg, J. M. "a Fluorescent Zinc Probe Based on Metal–Induced Peptide Folding," *J. Am. Chem. Soc.* 1996, 118, 6514.
Sundberg, S. A.; Barrett, R. W.; Pirrung, M., et al. "Spatially–Addressable Immobilization of Macromolecules on Solid Supports," *J. Am. Chem. Soc.* 1995, 117, 12050.
Holmes, C. P.; Adams, C. L.; Kochersperger, L. M., et al. "The Use of Light–Directed Combinatiorial Peptide Synthesis in Epitope Mapping," *Biopolymers* (*Peptide Science*) 1995, 37, 199.
Fodor, S. P. A.; Read, J. L.; Firrung, M.C., et al. "Light–Directed Spatially Addressable Parallel Chemical Synthesis," *Science* 1991, 251, 767.
Haughland, R. P.; Sheiner, R. F.; "Covalent Fluorescent Probes," In *Excited states of biopolymers*; Plenum, New York, 1983; p. 29.
Krizek, B. A.; Amann, B. T.; Kilfoil, V. J., et al. "A Consensus Zinc Finger Peptide: Design, High–Affinity Metal Binding, a pH–Dependent Structure, and a His to Cys Sequence Variant," *J. Am. Chem. Soc.* 1991, 113, 4518.

(List continued on next page.)

*Primary Examiner*—Jeffrey Snay
*Attorney, Agent, or Firm*—Brinks Hofer Gilson & Lione

[57] ABSTRACT

The present invention provides a selective fluorescent chemosensor, sensitive to nanomolar concentrations of zinc (II) and selective for this ion over $Na^+$, $Mg^{2+}$, $Co^{2+}$.

19 Claims, 3 Drawing Sheets

OTHER PUBLICATIONS

Jacobs, G. H. "Determination of the base recognition positions of zinc fingers from sequence analysis," *EMBO J.* 1992, 11, 4507.

Berg, J. M. "Zinc Finger Domains: Hypothesis and Current Knowledge," *Annual Reviews of Biophysics and Byophysical Chemistry* 1990, 19, 405.

Berg, J. M. "Zinc–finger Proteins," *Curr. Opin. Struct. Biol.* 1993, 3, 11.

Klevit, R. E.; Herriott, J. R.; Horvath S. J. "Solution Structure of a Zinc Finger Domain of Yeast ADR1," *Proteins: Struct. Func. Gen.* 1990, 7, 215.

Pavletich, N. P.; Pabo, C. O. "Zinc Finger–DNA Recognition: Crystal Structure of a Zif268–DNA Complex at 2.1 Å," *Science* 1991, 252, 809.

Fairall, L.; Schwabe, J. W. R.; Chapman, L., et al. "The crystal structure of two zinc finger peptides reveals an extension to the rules for zinc finger/DNA recognition," *Nature* 1993, 366, 483.

Lakowicz, J. R.; "Effects of Solvents on Fluorescence Emission Spectra," In *Principles of Fluorescence Spectroscopy*, Plenum Press. New York, 1983; p. 189.

Mukherhee, G. N.; Chattopadhyay, S. K. "Metal Complexes of some Model Peptide Derivatives. Part–IX. Complexation Equilibria of Cobalt–, Nickel–, Copper–and Zinc(II) with Salicyloylglycylglycine," *Indian Chem. Soc.* 1991, 68, 639.

Hulsbergen, F. B.; Reedijk, J. "Coordination compounds of tripeptides and pentapeptides containing L–histidyl residues," *Recl. Travl Chim Pays–Bas* 1993, 112, 278.

Ama, T.; Kawaghughi, H.; Uchijma, M., et al. "Metal Complexes of Peptides. Iv. Cobalt(III) Complexes with β–Alanyl–L–histidine (Carnosine) Functioning as a Quadridentate Ligand," *Bull Chem. Soc. Jpn.* 189, 62, 3464.

Patchornik, A.; Amit, B.; Woodward, R. B. "Photosensitive Protecting Groups," *J. Am. Chem. Soc.* 1970, 92, 6333.

Amit, B.; Zehavi, U.; Patchornik, A. "Photosensitive Protecting Groups of Amino Sugars and Their use in Glucoside Synthesis. 2–Nitrobenzyloxycarbonylamino and 6–Nitroveratryloxycarbonylamino Derivatives," *J. Org. Chem.* 1974, 39, 192.

Flanders, D. C.; Smith, H. I; Austin, S. "A new interferometric alignment technique," *Appl. Phys. Lett.* 1977, 31, 426.

Pless, J.; Bauer, W. "Boron Tris(trifluoroacetate) for Removal of Proteting Groups in Peptide Chemistry," *Angew. Chem. Int. Ed. Engl.* 1973, 12, 147.

Muller–Ackermann, E.; Panne, U.; Niessner, R. "A Fiber Optic Sensor Array for the Fluorimetric Detection of Heavy Metals," *Anal. Meth. I.* 1995, 2, 1982.

Camerman, N.; Camerman, A.; Sarkar, B. "Molecular design to mimic the copper(II) transport site of human albumin. The crystal and molecular structure of copper (II)–glycylglycyl–L–histidine–N–methyl amide monoaquo complex," *Can. J. Chem.* 1976, 54, 1309.

Hay, R. W.; Hassan, M. M.; You–Quan, C. "Kinetic and Thermodynamic Studies of Copper(II) and Nickel(II) Complexes of Glycylglycyl–L–Histidine," *J. Inorg. Bioch.* 1993, 52, 17.

Shullenberger, D. F.; Eason, P. D.; Long, E. C. "Design and Synthesis of a Versitile DNA–Cleaving Metallopeptide Structural Domain," *J. Am. Chem. Soc.* 1993, 115, 11038.

5,928,955

PEPTIDYL FLUORESCENT CHEMOSENSOR FOR DIVALENT ZINC

The U.S. Government has certain rights in this invention pursuant to Grant No. CHE 9412442 awarded by the National Science Foundation.

BACKGROUND OF THE INVENTION

1. Field of the Invention

The present invention provides a selective fluorescent chemosensor, sensitive to nanomolar concentrations of zinc (II), $Zn^{2+}$, a device containing the same, and methods for measuring the concentration of a metal in a sample using the device.

2. Discussion of the Background

The selective and quantitative detection of trace amounts of divalent zinc ($Zn^{2+}$) is commercially desirable for the diagnosis of metal ion induced disease states and in the protection of the environment. Zinc is an essential element which is present in the body at approximately 1 μmole/L. The USDA recommended dietary intake of $Zn^{2+}$ is only 15 mg/day, this provides an indication of how little $Zn^{2+}$ is required to maintain the required level of this element in a healthy adult.[1] Despite this relatively low concentration, $Zn^{2+}$ plays an essential role in biology and nutrition. Minor perturbations of normal $Zn^{2+}$ levels have been associated with retarded sexual maturation, stunted growth and skin damage. Over 99% of $Zn^{2+}$ in biological tissues and fluids is present in a chemically-combined form, with very little present as free $Zn^{2+}$ ion. Traditional methods such as atomic absorption effectively measure total $Zn^{2+}$ but can not distinguish between the chemically-combined and free forms. The problem of detecting free $Zn^{2+}$ is compounded because total free $Zn^{2+}$ is decreased only very slightly (50–100 pmol/$10^6$ cells) in cases of severe $Zn^{2+}$ deficiency.

The detection of $Zn^{2+}$ in the environment is also important, and is presently an intractable problem.[2] For example, interest in $Zn^{2+}$ concentrations in the ocean stems from its dual role as a required nanonutrient and as a potential toxic agent due to its widespread industrial and marine usage. Zinc exists at natural levels in ocean surface water at a total concentration of ca. 0.1 nM.[3] Dissolved $Zn^{2+}$ concentrations in seawater have been determined using atomic absorption spectrometry, mass spectrometry and voltammetry. The equipment for these procedures is shore based, time consuming and expensive. The concentration data are also inaccurate due to interference from other cations naturally present in sea water. A rapid, selective and more sensitive test for $Zn^{2+}$ concentrations which can be performed at sea is desirable.

The current technologies for selectively detecting free $Zn^{2+}$ in the presence of the chemically-combined forms have sensitivities in the micromolar range. For example, Zinquin[4] has a rather low sensitivity with association constants approximately 5 orders of magnitude weaker than many metal binding peptides and proteins.[5] In addition to its insensitivity, Zinquin cannot be used in the presence of copper.

There remains a need in the art for probes which have excellent sensivity for $Zn^{2+}$ and high selectivity for this element in the presence of other transition metal cations.

SUMMARY OF THE INVENTION

Accordingly, one object of this invention is to provide a selective fluorescent chemosensor, sensitive to nanomolar concentrations of a metal cation.

A second object of the present invention is to provide a device comprising the chemosensor and a detector.

A third object of the present invention is to provide a method for detecting the presence of a metal in a sample using such a device.

In light of the selectivity and avidity with which proteins bind Zn(II),[6] the present inventors used polypeptide architecture as the framework for metal ion recognition.[7] By manipulating synthetic polypeptides, the present inventors achieved the coordinated integration of fluorescent reporters for signal transduction within a metal binding peptidyl construct and obtained the chemosensor described herein. The present inventors have now developed a chemical probe which can provide direct, quantitative read-out of total free $Zn^{2+}$ concentrations in a fluid sample, either biological or seawater, similar to existing fiber optic sensors.[8]

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
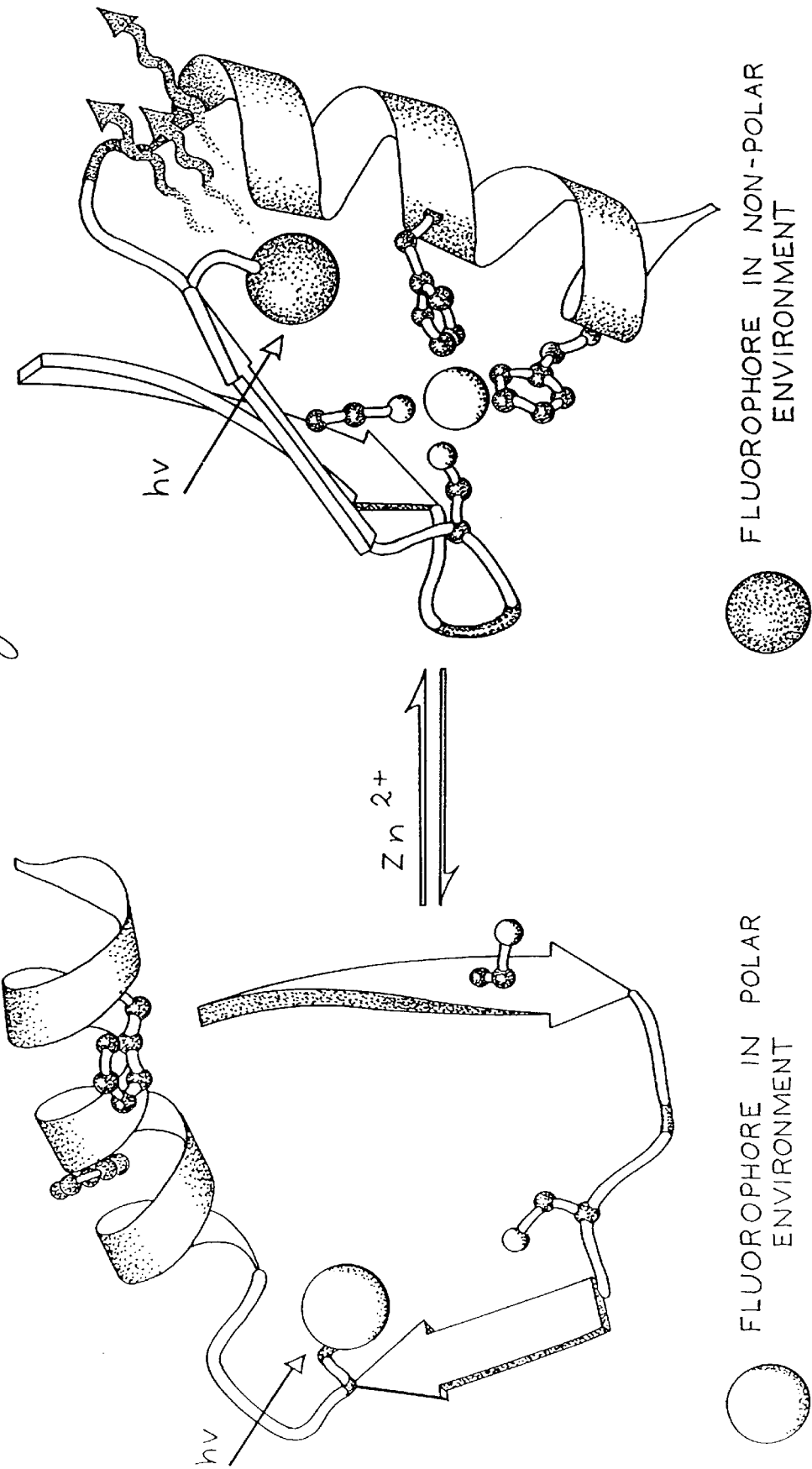
FIG. 1. Schematic of the chemosensor design. Metal binding induces peptide folding, shielding a fluorophore from solvent and increasing emission intensity.

The present invention comprises (i) a synthetic polypeptide template and (ii) a covalently attached fluorescent reporter that is sensitive to metal-induced conformational changes of the supporting framework, yet remote from the metal binding site. This approach combines the advantages of optical signalling[9] with the selective metal binding properties of an appropriate peptide. Furthermore, the modular design enables an approach wherein the fluorescent signalling mechanism is decoupled from the composition of the coordination sphere.

As used herein, the term free Zn refers to Zn ions which are available. The term chemically-combined refers to Zn that is tightly bound, or coordinated, to a competing ligand.
Metal Binding Peptide Templates Suitable metal binding peptide templates can be designed based on any naturally occurring metal binding protein. Preferred Zn binding peptidyl templates in accordance with the present invention are described in the following Table along with the protein they are components of and their SEQ ID NOs.

Human SP1

| | |
|---|---|
| QHICHI-QGCGKVYGKTSHLRAHLR--WHTG | (SEQ ID NO:1) |
| PFMCTW-SYCGKRFTRSDELQRHKR--THTG | (SEQ ID NO:2) |
| KFACPE---CPKRFMRSDHLSKHIK--THQN | (SEQ ID NO:3) |

Drosophila Serendipity b

| | |
|---|---|
| EIPCHI---CGEMFSSQEVLERHIKADTCQK | (SEQ ID NO:4) |
| QATCNV---CGLKVKDDEVLDLHMN--LHEG | (SEQ ID NO:5) |
| ELECRY---CDKKFSHKRNVLRHME--VHWD | (SEQ ID NO:6) |
| KYQCDK---CGERFSLSWLMYNHLM--RHDA | (SEQ ID NO:7) |
| ALICEV---CHQQFKTKRTYLHHLR--THQT | (SEQ ID NO:8) |
| -YPCPD---CEKSFVDKYTLKVHKR--VHQP | (SEQ ID NO:9) |

Drosophila Serendipity q

| | |
|---|---|
| KQECTT---CGKVYNSWYQLQKHLS-EEHSK | (SEQ ID NO:10) |
| NHICPI---CGVIRRDEEYLELHMN--LHEG | (SEQ ID NO:11) |
| EKQCRY---CPKSFSRPVNTLRHMR--SHWD | (SEQ ID NO:12) |
| KYQCEK---CGLRFSQDNLLYNHRL--RHEA | (SEQ ID NO:13) |
| PIICSI---CNVSFKSRKTFNHHTL--IHKE | (SEQ ID NO:14) |
| -HYCSV---CPKSFTERYTLKMHMK--THEG | (SEQ ID NO:15) |
| SGFCLI---CNTTFENKKELEHHLQ--FHAD | (SEQ ID NO:16) |

Drosophila Kruppel

| | |
|---|---|
| SFTCKI---CSRSFGYKHVLQNHER--THTG | (SEQ ID NO:17) |
| PFECPE---CDKRFTRDHHLKTHMR--LHTG | (SEQ ID NO:18) |
| PYHCSH---CDRQFVQVANLRRHLR--VHTG | (SEQ ID NO:19) |
| PYTCEI---CDGKFSDSNQLKSHML--VHTG | (SEQ ID NO:20) |
| PFECER---CHMKFRRRHHLMNHK----CGI | (SEQ ID NO:21) |

Drosophila Snail

| | |
|---|---|
| RFKCDE---CQKMYSTSMGLSKHRQ--FHCP | (SEQ ID NO:22) |
| THSCEE---CGKLYTTIGALKMHIR---HTL | (SEQ ID NO:23) |
| PCKCPI---CGKAFSRPWLLQGHIR--THTG | (SEQ ID NO:24) |
| PFQCPD---CPRSFADRSNLRAHQQ--TKVD | (SEQ ID NO:25) |
| KYACQV---CHKSFSRMSLLNKHSS-SNCTI | (SEQ ID NO:26) |

Xenopus Xfin

| | |
|---|---|
| SHHCPH---CKKSFVQRSDFLKHQR--THTG | (SEQ ID NO:27) |
| PYQCVE---CQKKFTERSALVNHQR--THTG | (SEQ ID NO:28) |
| PYTCLD---CQKTFNQRSALTKHRR--THTG | (SEQ ID NO:29) |
| PYRCSV---CSKSFIQNSDLVKHLR--THTG | (SEQ ID NO:30) |
| PYECPL---CVKRFAESSALMKHKR--THST | (SEQ ID NO:31) |
| PFRCSE---CSRSFTHNSDLTAHMR--KHTE | (SEQ ID NO:32) |
| PYSCSK---CRKTFKRWKSFLNHQQ--THSR | (SEQ ID NO:33) |
| PYLCSH---CNKGFIQNSDLVKHFR--THTG | (SEQ ID NO:34) |
| PYQCAE---CHKGFIQKSDLVKHLR--THTG | (SEQ ID NO:35) |
| PFKCSH---CDKKFTERSALAKHQR--THTG | (SEQ ID NO:36) |
| PYKCSD---CGKEFTQRSNLILHQR--IHTG | (SEQ ID NO:37) |
| PYKCTL---CDRTFIQNSDLVKHQK--VHAN | (SEQ ID NO:38) |
| PHKCSK---CDLTFSHWSTFMKHSK--LHSG | (SEQ ID NO:39) |
| KFQCAE---CKKGFTQKSDLVKHIR--VHTG | (SEQ ID NO:40) |
| PFKCLL---CKKSFSQNSDLHKHWR--IHTG | (SEQ ID NO:41) |
| PFPCYT---CDKSFTERSALIKHHR--THTG | (SEQ ID NO:42) |
| PHKCSV---CQKGFIQKSALTKHSR--THTG | (SEQ ID NO:43) |
| PYPCTQ---CGKSFIQNSDLVKHQR--IHTG | (SEQ ID NO:44) |
| PYHCTE---CNKRFTEGSSLVKHRR--THSG | (SEQ ID NO:45) |
| PYRCPQ---CEKTFIQSSDLVKHLV--VHNG | (SEQ ID NO:46) |
| PYPCTE---CGKVFHQRPALLKHLR--THKT | (SEQ ID NO:47) |
| RYPCNE---CSKEFFQTSDLVKHLR--THTG | (SEQ ID NO:48) |
| PYHCPE---CNKGFIQNSDLVKHQR--THTG | (SEQ ID NO:49) |
| PYTCSQ---CDKGFIQRSALTKHMR--THTG | (SEQ ID NO:50) |
| PYKCEQ---CQKCFIQNSDLVKHQR--IHTG | (SEQ ID NO:51) |
| PYHCPD---CDKRFTEGSSLIKHQR--IHSR | (SEQ ID NO:52) |
| PYPCGV---CGKSFSQSSNLLKHLK--CHSE | (SEQ ID NO:53) |
| SFKCND---CGKCFAHRSVLIKRVR--IHTG | (SEQ ID NO:54) |
| PYKCGL---CERSFVEKSALSRHQR--VHKN | (SEQ ID NO:55) |
| RYSCSE---CGKCFTHRSVFLKHWR--MHTG | (SEQ ID NO:56) |
| PYTCKE---CGKSFSQSSALVKHVR--IHTG | (SEQ ID NO:57) |
| PYACST---CGKSFIQKSDLAKHQR--IHTG | (SEQ ID NO:58) |
| PYTCTV---CGKKFIDRSSVVKHSR--THTG | (SEQ ID NO:59) |
| PYKCNE---CTKGFVQKSDLVKHMR--THTG | (SEQ ID NO:60) |
| PYGCNC---CDRSFSTHSASVRHQR--MCNT | (SEQ ID NO:61) |

Drosophila Terminus

| | |
|---|---|
| DLHCRR---CRTQFSRRSKLHIHQK-LRCGQ | (SEQ ID NO:62) |

Yeast SW15

| | |
|---|---|
| TFECLF-PGCTKTFKRRYNIRSHIQ--THLE | (SEQ ID NO:63) |
| PYSCDH-PGCDKAFVRNHDLIRHKK--SHQE | (SEQ ID NO:64) |
| -YACP----CGKKFNREDALVVHRSRMICSG | (SEQ ID NO:65) |

Xenopus transcription factor IIIA

| | |
|---|---|
| RYICSF-ADCGAAYNKNWKLQAHLC--KHTG | (SEQ ID NO:66) |
| PFPCKE-EGCEKGFTSLHHTLRHSL--THTG | (SEQ ID NO:67) |
| NFTCDS-DGCDLRFTTKANMKKHFN-RFHNI | (SEQ ID NO:68) |
| VYVCHF-ENCGKAFKKHNQLKVHQF--SHTQ | (SEQ ID NO:69) |
| PYECPH-EGCDKRFSLPSRLKRHEK--VHAG | (SEQ ID NO:70) |
| -YPCKKDDSCSFVGKTWTLYLKHVA-ECHQD | (SEQ ID NO:71) |
| -AVCDV---CNRKFRHKDYLRDHQK--THEK | (SEQ ID NO:72) |
| VYLCPR-DGCDRSYTTAFNLRSHIQ-SFHEE | (SEQ ID NO:73) |
| PFVCEH-AGCGKCFAMKKSLERHSV--VHDP | (SEQ ID NO:74) |

Yeast ADR1

| | |
|---|---|
| SFVCEV---CTRAFARQEHLKRHYR--SHTN | (SEQ ID NO:75) |
| PYPCGL---CNRCFTRRDLLIRHAQ--KIHSG | (SEQ ID NO:76) |

Drosophila KRH

| | |
|---|---|
| TYRCSE---CQREFELLAGLKKHLK--THRT | (SEQ ID NO:77) |
| KYQCDI---CGQKFVQKINLTHHAR--IHSS | (SEQ ID NO:78) |
| PYECPE---CQKRFQERSHLQRHQK--YHAQ | (SEQ ID NO:79) |
| SYRCEK---CGKMYKTERCLKVHNL--VHLE | (SEQ ID NO:80) |
| PFACTV---CDKSFISNSKLKQHSN--IHTG | (SEQ ID NO:81) |
| PFKCNY---CPRDFTNFPNWLKHTR-RRHKV | (SEQ ID NO:82) |

Mouse MKR1

| | |
|---|---|
| PFVCNY---CDKTFSFKSLLVSHKR--IHTG | (SEQ ID NO:83) |
| PYECDV---CGKTFSHKANLIKHQR--IHTG | (SEQ ID NO:84) |
| PFECPE---CGKAFTHQSNLIVHQR--AHME | (SEQ ID NO:85) |
| PYGCSE---CGKAFTHQSNLIVHQR--IHTG | (SEQ ID NO:86) |
| PYECNE---CAKTRRKKSNLIIHQK--IHTG | (SEQ ID NO:87) |
| RYECNE---CGKSFIQNSQLIIHRR--THTG | (SEQ ID NO:88) |
| PYECTE---CGKTFSQRSTLRLHLR--IHTG | (SEQ ID NO:89) |

Mouse MKR2

| | |
|---|---|
| VYGCDE---CGKTFRQSSILLKHQR--IHTG | (SEQ ID NO:90) |
| PYTCNV---CDKHFIERSSLTVHQR--THTG | (SEQ ID NO:91) |
| PYKCHE---CGKAFSQSMNLTVHQR--THTG | (SEQ ID NO:92) |
| PYQCKE---CGKAFRKNSSLIQHER--IHTG | (SEQ ID NO:93) |
| PYKCHD---CEKAFSKNSSLTQHRR--IHTG | (SEQ ID NO:94) |
| PYECMI---CGKHFTGRSSLTVHQR--IHTG | (SEQ ID NO:95) |
| PYECTE---CGKAFSQSAYLIEHRR--IHTG | (SEQ ID NO:96) |
| PYECDQ---CGKAFIKNSSLIVHQR--IHTG | (SEQ ID NO:97) |
| PYQCNE---CGKPFSRSTNLTRHQR--THT- | (SEQ ID NO:98) |

Drosophile Hunchback

| | |
|---|---|
| NYKCKT---CGVVAITKVDFWAHTR--THMK | (SEQ ID NO:99) |
| ILQCPK---CPFVTERKHHLEYHIR--KHKN | (SEQ ID NO:100) |
| PFQCDK---CSYTCVNKSMLNSHRK--SHSS | (SEQ ID NO:101) |
| QYRCAD---CDYATKYCHSFKLHLRHYGHKP | (SEQ ID NO:102) |
| IYECKY---CDIFFKDAVLYTIHMG--YHSC | (SEQ ID NO:103) |
| VFKCNM---CGEKCDGPVGLFVHMARNAHS- | (SEQ ID NO:104) |

Trypanosome TRS-1

| | |
|---|---|
| PTKCTE---CDATYQCRSSAVTHMV-NKHGF | (SEQ ID NO:105) |
| VLHCTI---CASKFAVPGRLLHHLR-TIHGI | (SEQ ID NO:106) |
| PFQCDL---CEASFGTHSSLSLHKK-LKHKS | (SEQ ID NO:107) |
| EVQCGV---CQKVLSCRDSLIRHCK-AFHKG | (SEQ ID NO:108) |
| MLVCPT---CGRQCASKTGLTLHQK-KMHGM | (SEQ ID NO:109) |

Mouse NGFI-A

| | |
|---|---|
| PYACPV-ESCDRRFSRSDELTRHIR--IHTG | (SEQ ID NO:110) |
| PFQCRI---CMRNFSRSDHLTTHIR--THTG | (SEQ ID NO:111) |
| PFACDI---CGRFARSDERKKRHTK--IKLR | (SEQ ID NO:112) |

Human ZFY

| | |
|---|---|
| VYPCMI---CGKKFKSRGFLKRHMK--NHPE | (SEQ ID NO:113) |
| KYHCTD---CDYTTNKKISLHNHLE--SHKL | (SEQ ID NO:114) |
| AIECDE---CGKHFSHAGALFTHKM--VHKE | (SEQ ID NO:115) |
| MHKCKF---CEYETAEQGLLNRHLL-AVHSK | (SEQ ID NO:116) |
| PHICVE---CGKGFRHPSELRKHMR--IHTG | (SEQ ID NO:117) |
| PYQCQY---CEYRSADSSNLKTHIK-TKHSK | (SEQ ID NO:118) |
| PFKCDI---CLLTFSDTKEVQQHTL--VHQE | (SEQ ID NO:119) |
| THQCLH---CDHKSSNSSDLKRHVI-SVHTK | (SEQ ID NO:120) |
| PHDCEM---CEKGFHRPSELKKHVA--VHKG | (SEQ ID NO:121) |
| MHQCRH---CDFKIADPFVLSRHIL-SVHTK | (SEQ ID NO:122) |
| PFRCKR---CRKGFRQQNELKKHMK--THSG | (SEQ ID NO:123) |
| VYQCEY---CEYSTTDASGFKRHVI-SIHTK | (SEQ ID NO:124) |
| PHRCEY---CKKGFRRPSEKNQHIM--RHHK | (SEQ ID NO:125) |

-continued

Xenopus P43 5S RNA binding protein

| | |
|---|---|
| LLRCPA-AGCKAFYRKEGKLQDHMA--GHSE | (SEQ ID NO:126) |
| PWKCGI-KDCDKVFARKRQILKHVK--RHLA | (SEQ ID NO:127) |
| KLSCPT-AGCKMTFSTKKSLSRHKL-YKHGE | (SEQ ID NO:128) |
| PLKCFV-PGCKRSFRKKRALRRHLS--VHSN | (SEQ ID NO:129) |
| LSVCDV-PGCSWKSSSVAKLVAHQK--RHRG | (SEQ ID NO:130) |
| -YRCSY-EGCQTVSPTWTALQTHVK--KHPL | (SEQ ID NO:131) |
| -LQCAA---CKKPFKKASALRRHKA--THAK | (SEQ ID NO:132) |
| QLPCPR-QDCDKTFSSVFNLTHHVARKLHLC | (SEQ ID NO:133) |
| THRCPH-SGCTRSFAMRESLLRHLV--VHDP | (SEQ ID NO:134) |

All amino acid sequences shown in the above table and throughout the specification are represented by the standard one-letter code for amino acids. A, alanine; C, cysteine; D, aspartic acid; E, glutamic acid; F, phenylalanine; G, glycine; H, histidine; I, isoleucine; K, lysine; L, leucine; M, methionine; N, asparagine; P, proline; Q, glutamine; R, arginine; S, serine; T, threonine; V, valine, W, tryptophan; Y, tyrosine. Dashes are present merely to allow alignment of the sequences.

The above Zn peptidyl templates can be designed based on known metal binding domains in zinc-fingers. A database with the sequence for 135 such domains appears in "A Consensus Zinc Finger Peptide: Design, High-Affinity Metal Binding, a pH-Dependent Structure, and a His to Cys Sequence Variant," Krizek et al., J. Am. Chem. Soc. 1991, 113, 4518; incorporated herein by reference. A database with 1340 zinc finger domains appears in GH Jacobs, EMBO J., 1992, 11, 4507–4517.

The metal binding domain of the zinc finger proteins shown above and described throughout the literature can be represented by the consensus sequence:[10,11]

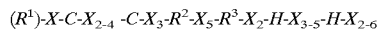

$(R^1)\text{-}X\text{-}C\text{-}X_{2\text{-}4}\text{ -}C\text{-}X_3\text{-}R^2\text{-}X_5\text{-}R^3\text{-}X_2\text{-}H\text{-}X_{3\text{-}5}\text{-}H\text{-}X_{2\text{-}6}$ Where X is any α-amino acid (both natural and synthetic) and the subscript refers to the number of residues at each location. The residues $R^1$–$R^3$ shown in bold in the above consensus sequence are known to form a hydrophobic core which contributes to the proper folding of the domain. These residues are preferably maintained as hydrophobic residues for high affinity binding. Suitable hydrophobic residues include Phe, Tyr, Leu, His, Ile, Val, etc. Preferably, $R^1$ is Phe or Tyr; $R^2$ is Phe and $R^3$ is Leu. However, as mentioned above, these residues can also be replaced with any α-amino acid. It is well established that the $R^1$, $R^2$, $R^3$ and X residues can be any α-amino acid; for example, each residue was replaced with an Ala and the domain of a zinc finger protein still folded properly and bound zinc.[12]

The peptidyl template can either consist of the whole domain shown above or a portion of those domains which bind Zn (herein referred to as the "Zn binding domain"). A Zn binding domain comprises at least 15 residues, preferably at least 20 residues, particularly preferably at least 25 residues, and may include the entire amino acid sequence of the Zn binding domain or, alternatively, a sequence comprised of at least those amino acid residues known to coordinate to Zn in their relative spatial array (the four residues in each sequence shown in bold text in the above Table).

That is, the Zn binding peptidyl template which is comprised of a portion of or the whole metal binding domain may contain amino acid substitutions within the natural sequence, so long as those substitutions do not totally destroy the Zn binding capacity of the domain. The selectivity and sensivity of the probe, that is its ability to detect free Zn versus chemically-combined Zn, can be conveniently varied by substituting non-coordinating amino acid residues.

The metal coordinating amino acids can be replaced with other metal coordinating amino acids. This provides a means for conveniently tuning the selectivity and sensitivity of the probe. Suitable metal coordinating amino acids include natural amino acids such as cysteine, histidine, aspartic acid, and glutamic acid. Alternatively, unnatural amino acid residues which bind metals can be used. A variety of such residues have recently been described in the literature, including bipyridal-alanine, and phenanthrolyl-alanine.

The Zn binding template may also comprise, in addition to a portion of, or the whole metal binding domain, attachments on the N- and/or C- termini. For example, the metal binding domain may be extended with either additional amino acids or organic blocking groups. Any number of amino acids can be used to extend the termini so long as the extension does not totally destroy the Zn binding capacity of the Zn binding domain. Preferably, the extensions at the N- and/or C-termini include the natural sequence of the metal binding protein surrounding the Zn binding domain. The primary sequences for each of the Zn binding domains in the above Table are known in the literature. The Zn binding template includes any fragment of the natural occurring protein which includes at least the Zn binding domain shown in the above Table.

Suitable organic groups useful for extending the N- and C-terminus include organic blocking groups which are known in the art and include, for example, amines, carboxylic acids, etc. Alternatively, the organic group can be a polyfunctional compound useful for linking the metal binding domain to a support or the support itself. Suitable solid supports and polylinkers are well described as are the means for attaching these to peptides.[14] Suitable solid supports include, for example, silicon, gold, glass and quartz.

Fluorescent Reporter

Suitable fluorescent reporter groups include any fluorescent group with photophysical properties that are sensitive to environment, such as:

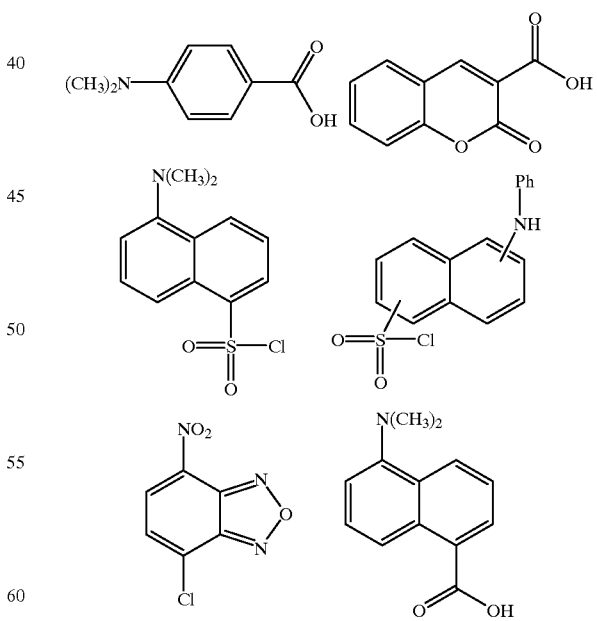

The above residues can be synthesized as described in the art.[15] Fluorophores are known to be polarity dependent as described in the literature.[16]

In the absence of divalent zinc, the zinc finger domains tend to be disordered. In contrast, when appropriate metal cations are present, coordination to the metal binding residues nucleates the formation of a defined tertiary structure including a cluster of conserved hydrophobic residues. To detect binding of a metal, the fluorophore is suitably placed within the sequence of the metal binding domain or at one of the ends. There is no limit to the distance between the fluorophore and the metal binding site provided that the metal binding event induces a significant change in the conformation of the polypeptide and causes the fluorophore to experience a new environment.

The fluorophore can be incorporated into the peptidyl template using conventional peptide synthesis techniques (see for example, M. Bodansky, Principles of Peptide Synthesis, Springer-Verlag: Berlin, 1984; Stewart & Young, Solid Phase Peptide Synthesis, Pierce: Rockford Ill., 1984; incorporated herein by reference). In general, residues containing a carboxylic acid, aryl chloride or a sulfonyl chloride group can be incorporated onto the N-terminus of the peptidyl template or, preferably, into any residue in the peptidyl template. For example, these fluorphores can be incorporated onto the side chain of a residue (for example, onto the amino group of a β-amino alanyl group).

As mentioned above, in the first embodiment of the invention, the present inventors examined $Zn^{2+}$ binding proteins. In the absence of metal ions, some $Zn^{2+}$ binding proteins are structurally disordered.[17] When $Zn^{2+}$ ions are present, coordination to cysteine and histidine residues nucleates the formation of a defined tertiary structure including a cluster of conserved hydrophobic residues (underlined in the above consensus sequence (I)).

For example in the first embodiment of their invention, the present inventors replaced one of the hydrophobic residues with a microenvironment-sensitive fluorophore to allow the monitoring of the metal binding event.[18] The fluorophore used was chosen to allow the selective elaboration of a side chain amine at variable positions within a synthetic polypeptide. That is, a differentially protected β-amino alanine (Baa) derivative, (S)-2,3-diamino-$N^{\alpha}$-9-fluorenylmethyl-oxycarbonyl-$N^{\beta}$-allyloxycarbonyl propanoic acid (Fmoc-L-Baa(alloc)-OH), was utilized. Compatibility of this residue with Fmoc solid phase peptide synthesis allows for orthogonal deprotection with a palladium catalyst.[19] The newly liberated amine is then available for fluorophore attachment, while leaving the remainder of the protected, peptide intact until the final resin deprotection.

Figure 4:
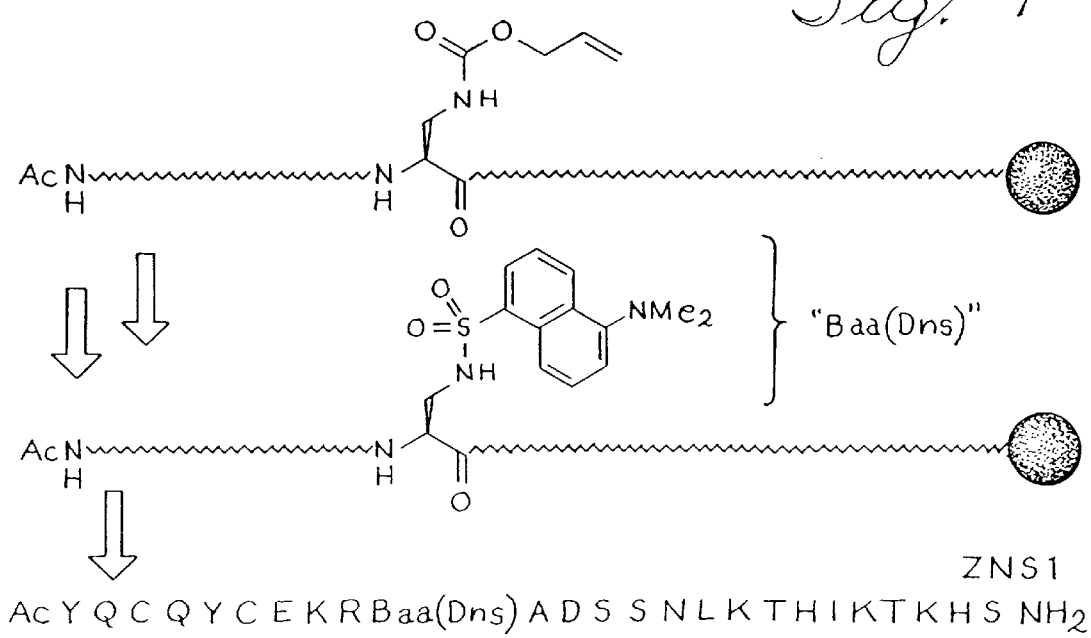
FIG. 4 is a schematic of the synthesis of peptide ZNS1.

As a first embodiment, the zinc finger domain "ZFY-swap"[20] was chosen as a template, and $Phe_{10}$ of that sequence was chosen as the site for replacement with the dansylated Baa amino acid derivative. As described below, the peptide ZNS1 was synthesized[21] FIG. 4 and assayed for the ability to selectively bind and report divalent zinc. The amino acid sequence of ZNS1 is (SEQ ID NO. 135):

Acetyl-Y Q CQYCEKRFADSSNLKTHIKTKHS-NH$_2$

The fluorophore was covalently attached to the Baa residue via an amide bond.

A solid Phase device

A solid phase device in accordance with the present invention comprises the chemosensor described above immobilized onto a solid support and a means for detecting fluorescence.

The peptidyl template with the incorporated fluorophore can be assembled by standard solid phase synthesis methods onto a solid phase as described above. A quartz surface is preferably used.

The solid phase immobilized chemosensor can then be integrated with a means for detecting fluorescence. A preferred means is a charge coupled device (CCD). This device can then be used to obtain direct read out of fluorescent emission from the chemosensor following selective irradiation at the appropriate wavelength of the fluorophore (usually in the range of 300–350 nm). Selective irradiation of the probe can be applied using fiber optics.[22]

Methods for detecting Zn(II)

Methods for detecting the presence of Zn in a sample will depend on the nature of the chemosensor.

If the chemosensor is in solution, the method comprises:
  contacting a sample with the chemosensor to form a test solution,
  irradiating the test solution at a wavelength sufficient to excite the fluorophore,
  measuring the fluorescence emission of the test solution, and
  determining the concentration of metal in said sample based on said fluorescence emission.

The amount of Zn in the sample can be quantified by comparing the measured fluorescence against a standard sample with known Zn(II) concentration.

Suitable samples include any aqueous solution including seawater, biological fluids such as plasma, blood, urine, etc.

In this embodiment of the method, the means for irradiating the sample and the means for measuring the fluorescence emission of the test solution are ideally performed by the same means—preferably a fluorometer. A wide range of fluorometers are commercially available.

If the chemosensor is immobilized onto a solid support as described above, the method of the present invention comprises:
  contacting the immobilized chemosensor with a sample,
  irradiating and measuring the fluorescent emission of said sample, and
  determining the concentration of metal in said sample based on said fluorescent emission.

Suitable samples are described above.

In this embodiment, the device provides the means for irradiating the sample and measuring the Zn(II) concentration in the sample.

Figure 2:
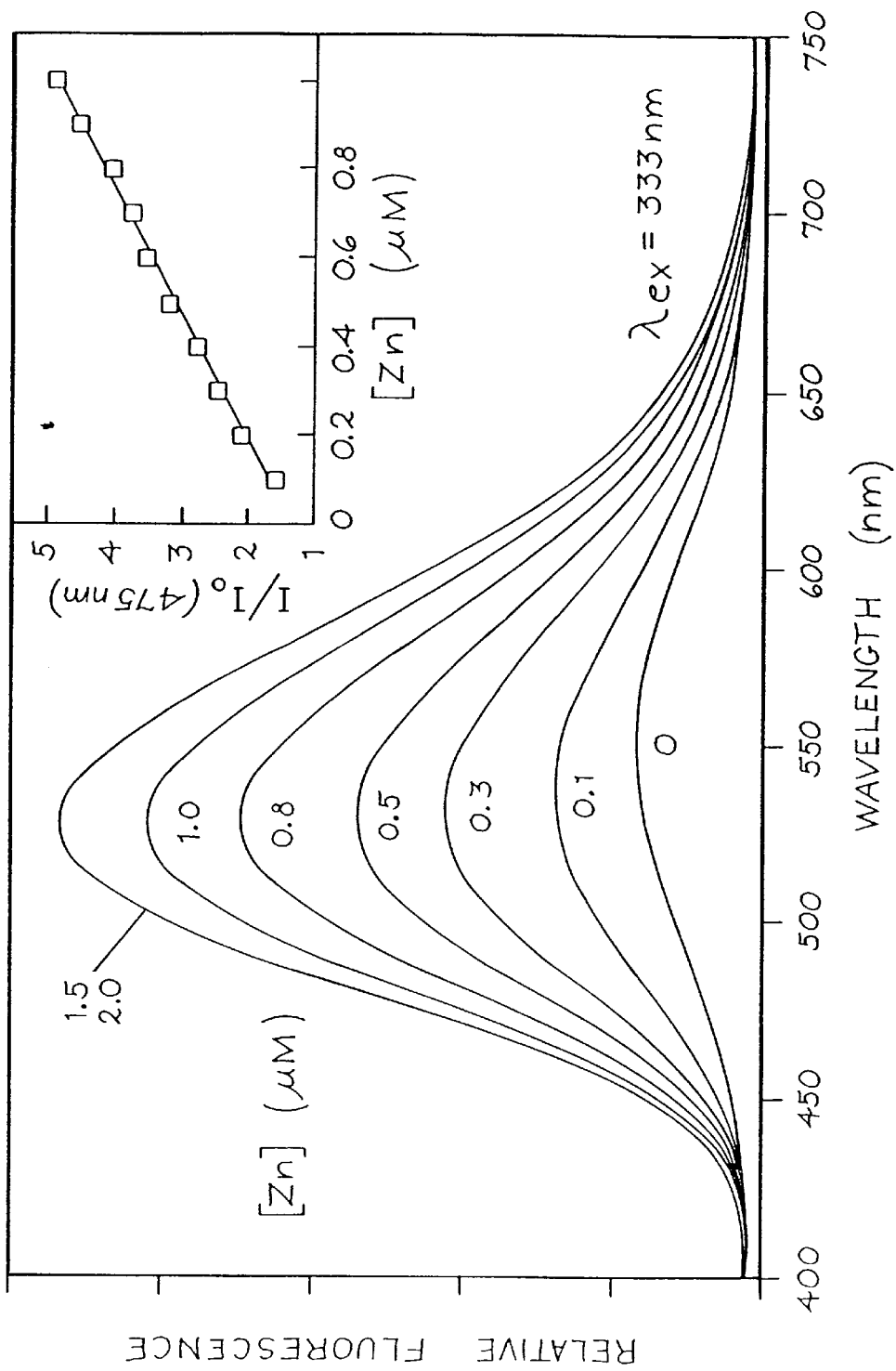
FIG. 2. Fluorescence emission response of ZNS1 to increasing levels of $Zn^{2+}$ (μM) in the presence of $Mg^{2+}$ (50 mM), and $Co^{2+}$ (100 μM) ions; excitation at 333 nm. Spectra were acquired with 1.4 μM ZNS1, 50 mM HEPES, pH 7.0, μ=0.5 (NaCl), 3.5 μM EDTA. Addition of EDTA was required to complex adventitious metal and establish the initial baseline prior to metal addition. The relative increase in fluorescence at 475 nm is linear between 0.1 and 1.0 μM $Zn^{2+}$.

In the first embodiment, the fluorescence emission properties of ZNS1 were sensitive to the presence of nanomolar concentrations of $Zn^{2+}$ (FIG. 2). The addition of $Zn^{2+}$ results in increased emission upon excitation of 333 nm, and the response (at 475 mn) is linear between 0.1 and 1 $\mu$M $Zn^{2+}$.[23] The chemosensor was selective for Zn(II) by a factor of $10^7$ over Na+, $10^6$ over $Mg^{2+}$ and $10^3$ over $Co^{2+}$.

Figure 3:
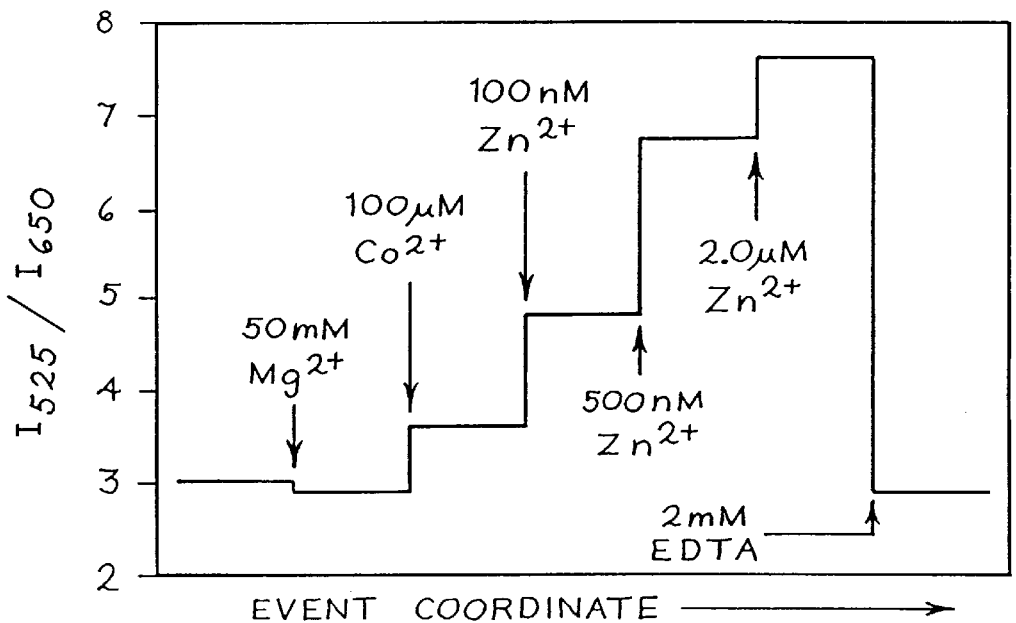
FIG. 3. Ratiometric analysis of the fluorescence emission changes upon the addition of various divalent metals. Initial conditions are 1.4 μM ZNS1, 50 mM HEPES, pH 7.0, 3.5 μM EDTA, μ=0.5 (NaCl). Arrows represent the addition of concentrated metal stocks to give the indicated composition.

As one important application of the zinc sensor is for the analysis of sea water, preliminary studies were also carried out in the presence of metal cations including 0.5 M Na+, 50 mM $Mg^{2+}$ and 100 $\mu$M $Co^{2+}$. The chemosensor is compatible with these competing species.[24] Due to a blue-shift which occurs upon metal binding, dual-wavelength ratiometric analysis of the fluorescence emission using 525 nm and 650 nm readings were used for $Zn^{2+}$ quantitation in solution.[25] An example of the response obtained by this method and the minimal effect of competing ions is shown in FIG. 3. The addition of EDTA to the complexed material demonstrates that the signalling mechanism of this peptide is readily reversible. The presence of two cysteine residues in ZNS1 makes it incompatible with ions such as $Cu^{2+}$, due to complications from dithiol oxidation. However, the modular nature of the design and the ready access to a variety of metal coordinating amino acids suggest strategies for remediating this limitation.

The first embodiment of the chemosensor is described in detail below and demonstrates the feasibility of exploiting metal-dependent structure modulation as the basis for trace analyte detection. ZNS1 shows excellent affinity for $Zn^{2+}$ relative to the chemical probe Zinquin.[26]

1. W. Kain and B. Schwederski in Bioinorganic Chemistry: Inorganic Elements in the Chemistry of Life Wiley, 1994.
2. R. B. Thompson and E. R. Jones, Anal. Chem. 1993, 65:730–734.
3. J. L. Nowicki et al, Anal. Chem. 1994, 66:2732–2738.
4. P. D. Zalewski et al., Biochem. J., 1993, 296:403–408.
5. P. D. Zalewski et al., Chemistry and Biology, 1994, 1:153–161.
6. Fraœsto da Silva et al., *The Biological Chemistry of the Elements*, Clarendon Press; New York, p. 561 (1993).
7. For a protein-based sensor that uses a diffusible fluorophore to report divalent zinc see (a) Thompson et al., Anal. Biochem., vol. 227, pp. 123–128 (1995); and (b) Thompson, Anal. Chem., vol. 65, pp. 730–734 (1993).
8. R. B. Thompson, Circuits and Devices, 1994:14–21.
9. Czarnik in Fluorescent Chemosensors for Ion and Molecule Recognition, ACS, Washington, D.C., pp. 1–9 (1993).
10. Berg, Acc. Chem. Res., vol. 28, pp. 14–19 (1995); Klug et al., FASEB J., vol. 9, pp. 597–604 (1995).
11. An alternate consensus sequence is observed for a subset of the zinc finger domains. M. A. Weiss et al, *Biochemistry*, vol.Ê29, pp. 5660–5664 (1990).
12. Michael et al., Proc. Natl. Acad. Sci. U.S.A., 1992, 89: 4796–4800.
14. For a review see, M.A. Gallop et al., J. Med. Chem., 1994, 37:1233–1251.
15. For a review see, R. P. Haugland, "Covalent Fluorescent Probes", In Excited States of Biopolymers, R. F. Steiner, Ed., Plenum Press: New York, 1983; incorporated herein by reference.
16. J. R. Lakowicz, Effects of Solvents on Fluorescence Emission, In "Principles of Fluorescence Spectroscopy", Plenum Press, New York, 1983; pp 189.
17. Frankel et al., Proc. Natl. Acad. Sci. U.S.A., vol. 84, pp. 4841–4845 (1987); Eis et al., Biochemistry, vol. 32, p. 7981 (1993).
18. Lakowicz in Principles of Fluorescence Spectroscopy, Plenum Press, New York, pp. 189–218 (1983).
19. Kates et al., Anal. Biochem., vol. 2/2, pp. 303–310 (1993).
20. Zinc finger domains with single residue replacements have been structurally characterized, showing the hydrophobic cluster is tolerant of substitution at position 10 (i.e., the second underlined residue in the consensus sequence). Weiss et al., Biochemistry, vol. 29, pp. 9808–9813 (1990).
21. The peptide was purified by reversed phase ($C_{18}$) HPLC. The identity of ZNS1 was confirmed by electrospray mass spec.
22. R. B. Thompson, Circuits & Devices, May 1994, 14–21.
23. CD and UV-vis metal titration experiments verify that ZNS1 binds $Co^{2+}$ with high affinity ($K_D$ 1–5 $\mu$M). Competition analysis in the presence of 1.5 $\mu$M $Zn^{2+}$ AND 100 $\mu$m $Co^{2+}$ reveals less than 5% change in the zinc-bound species, therefore the $K_D$ for $Zn^{2+}$ is <1 nM.
24. Bruland in Trace Elements in Sea Water; J. P. ÊRilet et al; Academic Press, London, pp. 157–220 (1975).
25. In the absence of metal ions the emission maximum is at 560 nm. The $Zn^{2+}$ complex has an emission maximum at 525 nm. Since these maxima are not widely separated, ratiometric analysis is carried out at 525 and 650 nm. This analysis normalizes data against bias from sources such as varying instrument response.
26. Zalewski et al., Chem. Bio., vol. 1, pp. 153–161 (1994).

Having generally described this invention, a further understanding can be obtained by reference to certain specific examples which are provided herein for purposes of illustration only and are not intended to be limiting unless otherwise specified.

EXAMPLES

Reagents used were purchased from Aldrich Chemical Co. or Fluka. Protected amino acid derivatives and reagents were obtained from Milligen (Perseptive) Biosearch, except FmocL-Baa(alloc)-OH which was synthesized as outlined below. Fluorescence experiments were performed on a SLM-Aminco SPF 500 c spectrofluorometer at ambient temperature. UV-Vis spectra were obtained on a Shimadzu UV160U, or a Beckman DU 7500 recording spectrophotometer.

All solutions and buffers employed in assays were composed of high-purity (18 $M\Omega cm^{-1}$) water obtained from a MILLI-Q (available from Millipore) deionization purification system, and were handled in acid-washed HDPE containers. To prevent metal catalyzed- and auto-oxidation of ZNS-1, buffer solutions were sparged with argon for one half hour then hydrogen for fifteen minutes immediately prior to use.

Metal titrations were performed by the addition of aliquots of concentrated stock solutions. The concentration of these stocks were determined by complexometric titrations performed in triplicate with standard EDTA solutions (Aldrich) and an appropriate colorometric indicator.[1]

Synthesis of Fmoc-L-Baa(alloc)-OH

The amino acid derivative (4) was synthesized from the precursor $N^\alpha$-Boc-L-$\beta$-amino alanine[2,3] via the route outlined in Scheme I.

Scheme 1
Strategy for the synthesis of Fmoc-Baa(alloc)-OH.

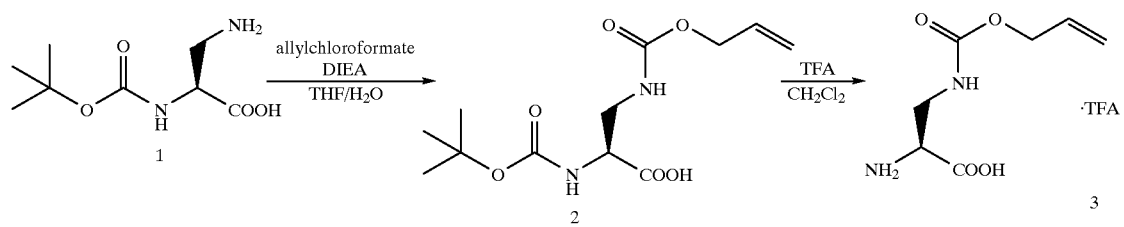

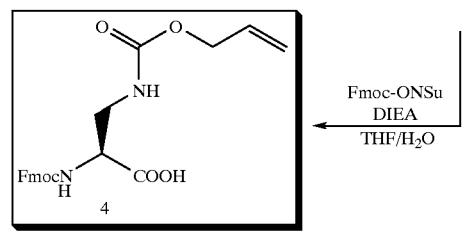

Boc-L-Baa(alloc)-OH (2) A solution of the Boc-amine (1) was prepared by dissolving 4.33 g (21.2 mmol) in 100 mL of 50% v/v THF in deionized water, assisted by sonication at 50° C. Sodium carbonate (2.46 g, 23.2 mmol) in 7 mL of water was added, and the resultant slurry was cooled to 0° C. with constant stirring. Allyl chloroformate (2.25 mL, 21.2 mmol) and diisopropyl-ethylamine (3.66 mL, 21.2 mmol) were added in alternating portions over a period of 20 minutes, after which the ice bath was removed and the reaction vessel let stir an additional 1.5 hr. The organic solvent was removed under reduced pressure, and additional deionized water added to increase the volume to 250 mL. Citric acid was added until pH 3.2, and the solution extracted with $CH_2Cl_2$ (5×200 mL). The organic layers were combined, dried over $MgSO_4$, and the solvent removed under reduced pressure to give a clear oil. Traces of contaminating lactam were separated by chromatography on silica gel (95:4:1, $CHCl_3$/MeOH/AcOH) to afford 4.60 g (75% yield) of a clear, colorless oil.

L-Baa(alloc)-OH.TFA (3) A 100-mL round bottom flask was charged with a stir bar, Boc-L-Baa(alloc)-OH (2, 4.55 g, 15.8 mmol), and $CH_2Cl_2$ (15 ML), then chilled to 0° C. with constant stirring. Trifluoroacetic acid (TFA, 10 mL, 130 mmol) was added drop wise over 15 minutes. After an additional 15 minutes the reaction was allowed to come up to room temperature and let stir for 2 hours. Excess TFA was removed under a stream of nitrogen, then the solvent was removed in vacuo to give a clear gum. Lyophilization of this residue from benzene gave 3 as a clear oil (4.63g, 97% yield).

Fmoc-L-Baa(alloc)-OH (4) The carbamate amine 3 (370 mg, 1.21 mmol) was dissolved in 2:1 $THF/H_2O$ (12 mL), requiring the assistance of vigorous stirring and sonication. Diisopropylethylamine (DIEA, 465 µL, 2.66 mmol) was added until the solution was slightly basic to litmus. Under vigorous stirring, N-(9-Fluorenylmethoxy-carbonyl)succinimide (FmocONSu, 816 mg, 2.42 mmol) was added in alternating portions with DIEA (420 µL, 2.42 mmol) over 30 minutes. The reaction was allowed to stir an additional four hours. The organic phase was removed in vacuo, and the remaining aqueous solution was increased in volume to –100 mL, and acidified with citric acid to pH 3. This was extracted with diethyl ether (2×50 mL), and the organic phase discarded. The aqueous phase was further extracted with $CH_2Cl_2$ (4×100 mL), the organic phases combined, dried over anhydrous $Na_2SO_4$, and concentrated under reduced pressure to afford a clear oil. Purification by silica gel chromatography (95:5:3 $CHCl_3$/MEOH/AcOH), followed by lyophilization from benzene gave 4 (465 mg, 96% yield) as a white powder.

Peptide synthesis

General. Peptides were synthesized on a Milligen 9050 peptide synthesizer at a 0.125 mmol scale. The support used was in all cases PAL-PEG-PS (Millipore) thus providing carboxyterminal primary amides. Couplings were performed at a concentration of 0.3 M acylating reagent and HOBT, in a volume sufficient to achieve a three-fold excess of amino acid to resin-bound acne. Pentafluorophenyl ester/1-hydroxybenzotriazole (Pfp/HOBT) chemistry was employed for all residues except Fmoc-L-Baa(alloc)-OH which was coupled by in situ active ester generation using HOBT/N,N'-diisopropyl-carbodiimide (HOBT/DIPCDI) activation. All coupling reactions were allowed to proceed for greater than 45 minutes, and were monitored for completion with the Enhanced Monitoring Opfion (EMO, Milligen). A coupling judged to be incomplete (<97%) was double coupled for an additional 45 minutes. After successful coupling cycles, any residual amines were acylated by a 10 min wash with 0.3M acetic anhydride/HOBT solution in 9:1 DMF/dichloromethane. Removal of the Fmoc group was performed with piperidine (20% v/v in DMF) with a standard wash duration of 7 minutes. This time was extended if an inefficient deblock was detected by EMO. After addition of the final residue, the amino-terminus was acetyl-capped (DMF/acetic anhydride/triethylamine, 4 mL:63 µL:94 µL) for 0.5 h then washed with DMF (5×10 mL) and MEOH (5×10 m). Residual solvent was removed under reduced pressure.

Alloc removal. The method of Kates et al.[4] was employed with some minor modifications. A typical procedure for removal of the alloc group was as follows. Under a blanket of nitrogen, a 20-mL plastic, stoppered vial was charged with resin from the completed peptide synthesis (300 mg, 0.21 meq/g, 63 µmol), and 5 mL of a solvent cocktail ($CHCl_3$ morpholine/AcOH, 90:5:5). The resin was allowed to swell 10 min, to which tetrakis(triphenyl-phosphine)palladium (200 mg, 173 µmol) was added under a blanket of nitrogen. The vial was capped, shielded from light, and placed on a wrist-action shaker at low speed for 2 h. The resin was filtered, washed with $CHCl_3$ (5×10 mL), and a palladiumchelating cocktail (DMF/diethyldithiocarbamic acid. $3H_2O$/triethylamine, 25 mL/225 mg/250 µL). Traces of this solution were removed with a basic wash (0.5% v/v triethylamine in DMF), and a final wash with methanol. The resin was transferred to a clean plastic vial, and the residual solvent removed under reduced pressure.

Dansyl coupling. Lyophilized resin taken directly from the alloc-removal procedure (280 mg, 0.21 meq/g, 59 µmol), was allowed to swell in DMF (5 mL). Dansyl chloride (159 mg, 590 µmol) was added, followed by triethylamine (82 mL, 590 µmol). The vial was capped under a blanket of nitrogen, and placed on a wrist-action shaker at low speed for 2 h. The resin was filtered, washed with a basic wash (5×10 mL, see above), washed with DMF (5×10 mL), then finally washed with MeOH (5 ×10 mL). The resin was transferred to a clean 20 mL polyethylene vial, and residual solvent was removed under reduced pressure prior to peptide cleavage.

Peptide cleavage acid purification. Peptides were cleaved after fluorophore coupling using 10 mL of Reagent K[5]

(trifluoroacetic acid/H$_2$O/ethanedithiol/thioanisole/phenol, 82.5/5/5/5/2.5) with a 2 h incubation period. The resin was filtered, concentrated to about 2 mL volume, and precipitated with ether/hexane 2:1 at −20° C. for 30 min. The supernatant was decanted, and the peptides triturated with ether/hexane 2/1 (5×50 mL). The resultant solid was resuspended in water (20 mL), lyophilized, and then purified by reverse phase (C$_{18}$) high performance liquid chromatography (HPLC), gradient elution with 0.1% v/v TFA in acetonitrile (solvent B) added to 0.1% v/v TFA in water (solvent A). The reduced (dithiol) and oxidized (intramolecular disulfide) forms of the peptide are separable by HPLC. Both forms of the peptide were collected and characterized, then combined and submitted together to a reduction protocol.

Peptide reduction The reduction was performed by dissolving the combined HPLC purified peptides in 0.1M phosphate buffer, pH 8.0, 50 MM dithiothreitol (DTT), 10 mM EDTA, 6M guanidine, and incubating at 25° C., 1 h. The reduction mixture was loaded onto a C$_{18}$ Sep-Pak (Millipore), and buffer salts and DTT were eluted with 10 mL water. The reduced peptide was eluted with 30% acetonitrile in water. Acetonitrile was removed from this solution under a stream of nitrogen until the sample could be frozen at 0° C., whence it was lyophilized. This was resuspended in high-purity water that had been sparged with argon 0.5 h then hydrogen 0.5 h. to delay oxidation. The resulting stock solution was periodically analyzed by HPLC and no significant (>2%) disulfide formation was detected.

The concentration of stock solutions ZNS-1 was determined by reaction with Eliman's reagent, 2,5'-dithiobis(2-nitrobenzoic acid) (DTNB)[6]. These assays were performed in triplicate, with excellent agreement (<5% error) between replicate runs. With this knowledge, the extinction coefficient of the dansyl chromophore was determined at 333 nm for ZNS-1 to be 5.3×10$^3$ M$^{-1}$ cm$^{-1}$ in 50 mM Hepes, pH 7.0. This value was used for all subsequent quantitations of ZNS-1.

Emission fluorescence assay. Assays were performed at pH 7.0 in 50 mM Hepes buffer, 0.5M NaCl in a stoppered 750 μL (1 cm×3 mm) quartz fluorometer cell. The concentration of ZNS-1 in a given assay was determined by measurement of the unique absorbance of the dansyl chromophore ($\epsilon$333 nm=5.3×10$^3$). Blank scans were taken against the same buffer immediately prior to ZNS-1 addition. Emission spectra were accumulated at I nm intervals with the following parameters: excitation wavelength =333 nm, emission wavelength =400–750 nm, excitation band pass 4 mm, emission band pass =2 mm, lamp potential =975 V, gain =10, filter (time constant) 3. To mask the effects of adventitious metal ions present prior to the initiation of metal titration, small aliquots of EDTA were added (in increments of 0.5 μM) until overlaying emission spectra were observed, and the wavelength of maximum emission was 560 nm. The EDTA concentration at the initiation of the metal titration was never in excess of 4 μM (<0.001% of the Mg$^{2+}$, and <4% of the CO$^{2+}$ subsequently added). With the concentrations of Zn$^{2+}$ and CO$^{2+}$ present over the course of a filtration, and the relative stability constants of EDTA for these species, at most 10% of the Zn$^{2+}$ would be complexed by EDTA.[7] Divalent metal ions were added to the assay from stock solutions prepared in unbuffered water. These included a 2.83M solution of MgCl$_2$, a 0.0969M solution of COCl$_2$, and a 100 PM solution of ZnCl$_2$.

REFERENCES

1. "Vogel's Textbook of Quantitative Inorganic Analysis;" Bassett, J.; Denney, R. C.; Jeffery, G. H. Mendham, J.; William Clowes: London, 1978; pp 223–402.
2. Arnold et al., J. Am. Chem. Soc. 1985, 107, 7105–9.
3. Kucharczyk et al., Synth. Comm. 1989, 19, 1603–1609.
4. Kates et al., Anal. Biochem. 1993, 212, 303–310.
5. King et al., Int. J. Pept. Protein Res. 1990, 36, 255–266.
6. Riddles et al., Meth. Enzymol. 1983, 91, 49–60.
7. O'Sullivan & Smithers, Meth. Enzymol. 1979, 63, 294.

Obviously, numerous modifications and variations of the present invention are possible in light of the above teachings. It is therefore to be understood that within the scope of the appended claims, the invention may be practiced otherwise than as specifically described herein.

---

What is claimed as new and desired to be secured by Letters Patent of the United States is:

1. A sensor for measuring the concentration of zinc(II) in a sample, comprising:
   (i) a peptide template comprised of a Zn(II) binding domain of a Zn(II) binding protein, wherein said template is covalently attached to
   (ii) a fluorescent reporting group.

2. The sensor of claim 1, wherein said Zn(II) binding protein is a zinc finger protein.

3. The sensor of claim 1, wherein said Zn(II) binding domain is of the formula:

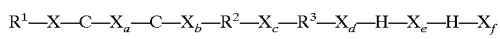

wherein
   a is 2, 3 or 4;
   b is 1, 2 or 3;
   c is 1, 2, 3, 4 or 5;
   d is 1 or 2;
   e is 3, 4 or 5;
   f is 2, 3, 4, 5 or 6; and
   $R^1$, $R^2$, $R^3$ and each X are, independently, an α-amino acid.

4. The sensor of claim 3, wherein $R^1$, $R^2$ and $R^3$ are, independently, a hydrophobic α-amino acid.

5. The sensor of claim 4, wherein $R^1$, $R^2$ and $R^3$ are, independently, Phe, Tyr, Leu, Ile, His or Val.

6. The sensor of claim 3, wherein said zinc (II) binding domain has an amino acid sequence selected from SEQ ID NO:1–135.

7. The sensor of claim 6, wherein said zinc (II) binding domain has an amino acid sequence of SEQ ID NO:135.

8. The sensor of claim 1, wherein said fluorescent reporter group is covalently attached to the N- or C-terminus of the peptidyl template.

9. The sensor of claim 1, wherein said fluorescent reporter group is covalently attached to a side chain of an amino acid residue in the peptidyl template.

10. The sensor of claim 3, wherein $R^1$, $R^2$ or $R^3$ is an amino acid residue covalently attached to said fluorescent reporter group.

11. The sensor of claim 10, wherein $R^2$ is

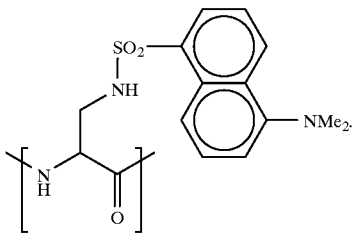

12. The sensor of claim 7, wherein $Phe_{10}$ is replaced with a residue of the formula:

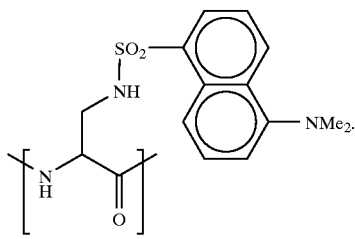

13. A device comprising:
the chemosensor of claim 1, and a fluorescence detector.

14. A device comprising:
the chemosensor of claim 1 immobilized onto a solid support,
a means for irradiating the chemosensor,
and a means for detecting the fluorescence emission of said chemosensor.

15. The device of claim 14, wherein said sensor is immobilized onto said solid support via the N-terminus of said peptidyl template.

16. The device of claim 14, wherein said solid support is gold, quartz, silicon or glass.

17. The device of claim 14, wherein said means for detecting fluoresence is a charged coupled device.

18. A method for measuring the concentration of Zn(II) in a sample, comprising the steps of:
contacting the device of claim 13 with a sample,
irradiating the sample at a wavelength sufficient to excite the fluorophore,
measuring the fluorescent emission of said sample, and
determining the concentration of metal in said sample based on said fluorescence emission.

19. A method for measuring the concentration of ZN(II) in a sample, comprising the steps of:
contacting the device of claim 14 with a sample,
irradiating the sample at a wavelength sufficient to excite the fluorophore,
measuring the fluorescence emission of said sample, and
determining the concentration of metal in said sample based on said fluorescence emission.

* * * * *

SEQUENCE LISTING (1) GENERAL INFORMATION:

(iii) NUMBER OF SEQUENCES: 136

(2) INFORMATION FOR SEQ ID NO:1:

(i) SEQUENCE CHARACTERISTICS:
      (A) LENGTH: 28 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:1:

```
Gln His Ile Cys His Ile Gln Gly Cys Gly Lys Val Tyr Gly Lys Thr
1               5                   10                  15

Ser His Leu Arg Ala His Leu Arg Trp His Thr Gly
            20                  25
```

(2) INFORMATION FOR SEQ ID NO:2:

(i) SEQUENCE CHARACTERISTICS:
    (A) LENGTH: 28 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:2:

Pro Phe Met Cys Thr Trp Ser Tyr Cys Gly Lys Arg Phe Thr Arg Ser
1               5                   10                  15

Asp Glu Leu Gln Arg His Lys Arg Thr His Thr Gly
            20                  25

(2) INFORMATION FOR SEQ ID NO:3:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

Lys Phe Ala Cys Pro Glu Cys Pro Lys Arg Phe Met Arg Ser Asp His
1               5                   10                  15

Leu Ser Lys His Ile Lys Thr His Gln Asn
            20                  25

(2) INFORMATION FOR SEQ ID NO:4:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

Glu Ile Pro Cys His Ile Cys Gly Glu Met Phe Ser Ser Gln Glu Val
1               5                   10                  15

Leu Glu Arg His Ile Lys Ala Asp Thr Cys Gln Lys
            20                  25

(2) INFORMATION FOR SEQ ID NO:5:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

Gln Ala Thr Cys Asn Val Cys Gly Leu Lys Val Lys Asp Asp Glu Val
1               5                   10                  15

Leu Asp Leu His Met Asn Leu His Glu Gly
            20                  25

(2) INFORMATION FOR SEQ ID NO:6:

(i) SEQUENCE CHARACTERISTICS:
        (A) LENGTH: 26 amino acids
        (B) TYPE: amino acid
        (C) STRANDEDNESS:

(D) TOPOLOGY: linear (ii) MOLECULE TYPE: peptide (xi) SEQUENCE DESCRIPTION: SEQ ID NO:6:

Glu Leu Glu Cys Arg Tyr Cys Asp Lys Lys Phe Ser His Lys Arg Asn
1               5                   10                  15

Val Leu Arg His Met Glu Val His Trp Asp
            20                  25

(2) INFORMATION FOR SEQ ID NO:7:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:

Lys Tyr Gln Cys Asp Lys Cys Gly Glu Arg Phe Ser Leu Ser Trp Leu
1               5                   10                  15

Met Tyr Asn His Leu Met Arg His Asp Ala
            20                  25

(2) INFORMATION FOR SEQ ID NO:8:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

Ala Leu Ile Cys Glu Val Cys His Gln Gln Phe Lys Thr Lys Arg Thr
1               5                   10                  15

Tyr Leu His His Leu Arg Thr His Gln Thr
            20                  25

(2) INFORMATION FOR SEQ ID NO:9:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

Tyr Pro Cys Pro Asp Cys Glu Lys Ser Phe Val Asp Lys Tyr Thr Leu
1               5                   10                  15

Lys Val His Lys Arg Val His Gln Pro
            20                  25

(2) INFORMATION FOR SEQ ID NO:10:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

Lys Gln Glu Cys Thr Thr Cys Gly Lys Val Tyr Asn Ser Trp Tyr Gln
1               5                   10                  15

Leu Gln Lys His Leu Ser Glu Glu His Ser Lys
            20                  25

(2) INFORMATION FOR SEQ ID NO:11:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:11:

Asn His Ile Cys Pro Ile Cys Gly Val Ile Arg Arg Asp Glu Glu Tyr
1               5                   10                  15

Leu Glu Leu His Met Asn Leu His Glu Gly
            20                  25

(2) INFORMATION FOR SEQ ID NO:12:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:12:

Glu Lys Gln Cys Arg Tyr Cys Pro Lys Ser Phe Ser Arg Pro Val Asn
1               5                   10                  15

Thr Leu Arg His Met Arg Ser His Trp Asp
            20                  25

(2) INFORMATION FOR SEQ ID NO:13:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

Lys Tyr Gln Cys Glu Lys Cys Gly Leu Arg Phe Ser Gln Asp Asn Leu
1               5                   10                  15

Leu Tyr Asn His Arg Leu Arg His Glu Ala
            20                  25

(2) INFORMATION FOR SEQ ID NO:14:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:14:

Pro Ile Ile Cys Ser Ile Cys Asn Val Ser Phe Lys Ser Arg Lys Thr
1               5                   10                  15

```
        Phe Asn His His Thr Leu Ile His Lys Glu
                         20                  25
```

(2) INFORMATION FOR SEQ ID NO:15:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:15:

```
        His Tyr Cys Ser Val Cys Pro Lys Ser Phe Thr Glu Arg Tyr Thr Leu
        1               5                   10                  15

Lys Met His Met Lys Thr His Glu Gly
                         20                  25
```

(2) INFORMATION FOR SEQ ID NO:16:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:16:

```
        Ser Gly Phe Cys Leu Ile Cys Asn Thr Thr Phe Glu Asn Lys Lys Glu
        1               5                   10                  15

Leu Glu His His Leu Gln Phe His Ala Asp
                         20                  25
```

(2) INFORMATION FOR SEQ ID NO:17:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:17:

```
        Ser Phe Thr Cys Lys Ile Cys Ser Arg Ser Phe Gly Tyr Lys His Val
        1               5                   10                  15

Leu Gln Asn His Glu Arg Thr His Thr Gly
                         20                  25
```

(2) INFORMATION FOR SEQ ID NO:18:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:18:

```
        Pro Phe Glu Cys Pro Glu Cys Asp Lys Arg Phe Thr Arg Asp His His
        1               5                   10                  15

Leu Lys Thr His Met Arg Leu His Thr Gly
                         20                  25
```

(2) INFORMATION FOR SEQ ID NO:19:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:19:

```
Pro Tyr His Cys Ser His Cys Asp Arg Gln Phe Val Gln Val Ala Asn
1               5                   10                  15

Leu Arg Arg His Leu Arg Val His Thr Gly
            20                  25
```

(2) INFORMATION FOR SEQ ID NO:20:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:20:

```
Pro Tyr Thr Cys Glu Ile Cys Asp Gly Lys Phe Ser Asp Ser Asn Gln
1               5                   10                  15

Leu Lys Ser His Met Leu Val His Thr Gly
            20                  25
```

(2) INFORMATION FOR SEQ ID NO:21:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:21:

```
Pro Phe Glu Cys Glu Arg Cys His Met Lys Phe Arg Arg Arg His His
1               5                   10                  15

Leu Met Asn His Lys Cys Gly Ile
            20
```

(2) INFORMATION FOR SEQ ID NO:22:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:22:

```
Arg Phe Lys Cys Asp Glu Cys Gln Lys Met Tyr Ser Thr Ser Met Gly
1               5                   10                  15

Leu Ser Lys His Arg Gln Phe His Cys Pro
            20                  25
```

(2) INFORMATION FOR SEQ ID NO:23:

(i) SEQUENCE CHARACTERISTICS:

(A) LENGTH: 25 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:23:

Thr His Ser Cys Glu Glu Cys Gly Lys Leu Tyr Thr Thr Ile Gly Ala
    1               5                   10                  15

Leu Lys Met His Ile Arg His Thr Leu
                20                  25

(2) INFORMATION FOR SEQ ID NO:24:

(i) SEQUENCE CHARACTERISTICS:
            (A) LENGTH: 26 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:24:

Pro Cys Lys Cys Pro Ile Cys Gly Lys Ala Phe Ser Arg Pro Trp Leu
    1               5                   10                  15

Leu Gln Gly His Ile Arg Thr His Thr Gly
                20                  25

(2) INFORMATION FOR SEQ ID NO:25:

(i) SEQUENCE CHARACTERISTICS:
            (A) LENGTH: 26 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:25:

Pro Phe Gln Cys Pro Asp Cys Pro Arg Ser Phe Ala Asp Arg Ser Asn
    1               5                   10                  15

Leu Arg Ala His Gln Gln Thr His Val Asp
                20                  25

(2) INFORMATION FOR SEQ ID NO:26:

(i) SEQUENCE CHARACTERISTICS:
            (A) LENGTH: 27 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:26:

Lys Tyr Ala Cys Gln Val Cys His Lys Ser Phe Ser Arg Met Ser Leu
    1               5                   10                  15

Leu Asn Lys His Ser Ser Ser Asn Cys Thr Ile
                20                  25

(2) INFORMATION FOR SEQ ID NO:27:

(i) SEQUENCE CHARACTERISTICS:
            (A) LENGTH: 26 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:27:

Ser His His Cys Pro His Cys Lys Lys Ser Phe Val Gln Arg Ser Asp
1               5                   10                  15

Phe Leu Lys His Gln Arg Thr His Thr Gly
            20                  25

(2) INFORMATION FOR SEQ ID NO:28:

(i) SEQUENCE CHARACTERISTICS:
       (A) LENGTH: 26 amino acids
       (B) TYPE: amino acid
       (C) STRANDEDNESS:
       (D) TOPOLOGY: linear (ii) MOLECULE TYPE: peptide (xi) SEQUENCE DESCRIPTION: SEQ ID NO:28:

Pro Tyr Gln Cys Val Glu Cys Gln Lys Phe Thr Glu Arg Ser Ala
1               5                   10                  15

Leu Val Asn His Gln Arg Thr His Thr Gly
            20                  25

(2) INFORMATION FOR SEQ ID NO:29:

(i) SEQUENCE CHARACTERISTICS:
       (A) LENGTH: 26 amino acids
       (B) TYPE: amino acid
       (C) STRANDEDNESS:
       (D) TOPOLOGY: linear (ii) MOLECULE TYPE: peptide (xi) SEQUENCE DESCRIPTION: SEQ ID NO:29:

Pro Tyr Thr Cys Leu Asp Cys Gln Lys Thr Phe Asn Gln Arg Ser Ala
1               5                   10                  15

Leu Thr Lys His Arg Arg Thr His Thr Gly
            20                  25

(2) INFORMATION FOR SEQ ID NO:30:

(i) SEQUENCE CHARACTERISTICS:
       (A) LENGTH: 26 amino acids
       (B) TYPE: amino acid
       (C) STRANDEDNESS:
       (D) TOPOLOGY: linear (ii) MOLECULE TYPE: peptide (xi) SEQUENCE DESCRIPTION: SEQ ID NO:30:

Pro Tyr Arg Cys Ser Val Cys Ser Lys Ser Phe Ile Gln Asn Ser Asp
1               5                   10                  15

Leu Val Lys His Leu Arg Thr His Thr Gly
            20                  25

(2) INFORMATION FOR SEQ ID NO:31:

(i) SEQUENCE CHARACTERISTICS:
       (A) LENGTH: 26 amino acids
       (B) TYPE: amino acid
       (C) STRANDEDNESS:
       (D) TOPOLOGY: linear (ii) MOLECULE TYPE: peptide (xi) SEQUENCE DESCRIPTION: SEQ ID NO:31:

```
        Pro Tyr Glu Cys Pro Leu Cys Val Lys Arg Phe Ala Glu Ser Ser Ala
        1               5                   10                  15

Leu Met Lys His Lys Arg Thr His Ser Thr
                    20                  25
```

(2) INFORMATION FOR SEQ ID NO:32:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:32:

```
        Pro Phe Arg Cys Ser Glu Cys Ser Arg Ser Phe Thr His Asn Ser Asp
        1               5                   10                  15

Leu Thr Ala His Met Arg Lys His Thr Glu
                    20                  25
```

(2) INFORMATION FOR SEQ ID NO:33:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:33:

```
        Pro Tyr Ser Cys Ser Lys Cys Arg Lys Thr Phe Lys Arg Trp Lys Ser
        1               5                   10                  15

Phe Leu Asn His Gln Gln Thr His Ser Arg
                    20                  25
```

(2) INFORMATION FOR SEQ ID NO:34:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:34:

```
        Pro Tyr Leu Cys Ser His Cys Asn Lys Gly Phe Ile Gln Asn Ser Asp
        1               5                   10                  15

Leu Val Lys His Phe Arg Thr His Thr Gly
                    20                  25
```

(2) INFORMATION FOR SEQ ID NO:35:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:35:

```
        Pro Tyr Gln Cys Ala Glu Cys His Lys Gly Phe Ile Gln Lys Ser Asp
        1               5                   10                  15
```

```
    Leu Val Lys His Leu Arg Thr His Thr Gly
                20                  25
```

(2) INFORMATION FOR SEQ ID NO:36:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:36:

```
    Pro Phe Lys Cys Ser His Cys Asp Lys Phe Thr Glu Arg Ser Ala
    1               5                   10                  15

Leu Ala Lys His Gln Arg Thr His Thr Gly
                20                  25
```

(2) INFORMATION FOR SEQ ID NO:37:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:37:

```
    Pro Tyr Lys Cys Ser Asp Cys Gly Lys Glu Phe Thr Gln Arg Ser Asn
    1               5                   10                  15

Leu Ile Leu His Gln Arg Ile His Thr Gly
                20                  25
```

(2) INFORMATION FOR SEQ ID NO:38:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:38:

```
    Pro Tyr Lys Cys Thr Leu Cys Asp Arg Thr Phe Ile Gln Asn Ser Asp
    1               5                   10                  15

Leu Val Lys His Gln Lys Val His Ala Asn
                20                  25
```

(2) INFORMATION FOR SEQ ID NO:39:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:39:

```
    Pro His Lys Cys Ser Lys Cys Asp Leu Thr Phe Ser His Trp Ser Thr
    1               5                   10                  15

Phe Met Lys His Ser Lys Leu His Ser Gly
                20                  25
```

(2) INFORMATION FOR SEQ ID NO:40:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:40:

```
Lys Phe Gln Cys Ala Glu Cys Lys Lys Gly Phe Thr Gln Lys Ser Asp
 1               5                  10                  15

Leu Val Lys His Ile Arg Val His Thr Gly
            20                  25
```

(2) INFORMATION FOR SEQ ID NO:41:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:41:

```
Pro Phe Lys Cys Leu Leu Cys Lys Lys Ser Phe Ser Gln Asn Ser Asp
 1               5                  10                  15

Leu His Lys His Trp Arg Ile His Thr Gly
            20                  25
```

(2) INFORMATION FOR SEQ ID NO:42:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:42:

```
Pro Phe Pro Cys Tyr Thr Cys Asp Lys Ser Phe Thr Glu Arg Ser Ala
 1               5                  10                  15

Leu Ile Lys His His Arg Thr His Thr Gly
            20                  25
```

(2) INFORMATION FOR SEQ ID NO:43:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:43:

```
Pro His Lys Cys Ser Val Cys Gln Lys Gly Phe Ile Gln Lys Ser Ala
 1               5                  10                  15

Leu Thr Lys His Ser Arg Thr His Thr Gly
            20                  25
```

(2) INFORMATION FOR SEQ ID NO:44:

(i) SEQUENCE CHARACTERISTICS:
        (A) LENGTH: 26 amino acids

```
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:44:

Pro Tyr Pro Cys Thr Gln Cys Gly Lys Ser Phe Ile Gln Asn Ser Asp
    1               5                   10                  15

Leu Val Lys His Gln Arg Ile His Thr Gly
                20                  25

(2) INFORMATION FOR SEQ ID NO:45:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:45:

Pro Tyr His Cys Thr Glu Cys Asn Lys Arg Phe Thr Glu Gly Ser Ser
    1               5                   10                  15

Leu Val Lys His Arg Arg Thr His Ser Gly
                20                  25

(2) INFORMATION FOR SEQ ID NO:46:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:46:

Pro Tyr Arg Cys Pro Gln Cys Glu Lys Thr Phe Ile Gln Ser Ser Asp
    1               5                   10                  15

Leu Val Lys His Leu Val Val His Asn Gly
                20                  25

(2) INFORMATION FOR SEQ ID NO:47:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:47:

Pro Tyr Pro Cys Thr Glu Cys Gly Lys Val Phe His Gln Arg Pro Ala
    1               5                   10                  15

Leu Leu Lys His Leu Arg Thr His Lys Thr
                20                  25

(2) INFORMATION FOR SEQ ID NO:48:

(i) SEQUENCE CHARACTERISTICS:
        (A) LENGTH: 26 amino acids
        (B) TYPE: amino acid
        (C) STRANDEDNESS:
        (D) TOPOLOGY: linear
```

(ii) MOLECULE TYPE: peptide (xi) SEQUENCE DESCRIPTION: SEQ ID NO:48:

Arg Tyr Pro Cys Asn Glu Cys Ser Lys Glu Phe Phe Gln Thr Ser Asp
    1               5                   10                  15

Leu Val Lys His Leu Arg Thr His Thr Gly
                20                  25

(2) INFORMATION FOR SEQ ID NO:49:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:49:

Pro Tyr His Cys Pro Glu Cys Asn Lys Gly Phe Ile Gln Asn Ser Asp
    1               5                   10                  15

Leu Val Lys His Gln Arg Thr His Thr Gly
                20                  25

(2) INFORMATION FOR SEQ ID NO:50:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:50:

Pro Tyr Thr Cys Ser Gln Cys Asp Lys Gly Phe Ile Gln Arg Ser Ala
    1               5                   10                  15

Leu Thr Lys His Met Arg Thr His Thr Gly
                20                  25

(2) INFORMATION FOR SEQ ID NO:51:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:51:

Pro Tyr Lys Cys Glu Gln Cys Gln Lys Cys Phe Ile Gln Asn Ser Asp
    1               5                   10                  15

Leu Val Lys His Gln Arg Ile His Thr Gly
                20                  25

(2) INFORMATION FOR SEQ ID NO:52:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:52:

```
    Pro Tyr His Cys Pro Asp Cys Asp Lys Arg Phe Thr Glu Gly Ser Ser
    1               5                   10                  15

Leu Ile Lys His Gln Arg Ile His Ser Arg
                    20                  25
```

(2) INFORMATION FOR SEQ ID NO:53:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:53:

```
    Pro Tyr Pro Cys Gly Val Cys Gly Lys Ser Phe Ser Gln Ser Ser Asn
    1               5                   10                  15

Leu Leu Lys His Leu Lys Cys His Ser Glu
                    20                  25
```

(2) INFORMATION FOR SEQ ID NO:54:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:54:

```
    Ser Phe Lys Cys Asn Asp Cys Gly Lys Cys Phe Ala His Arg Ser Val
    1               5                   10                  15

Leu Ile Lys His Val Arg Ile His Thr Gly
                    20                  25
```

(2) INFORMATION FOR SEQ ID NO:55:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:55:

```
    Pro Tyr Lys Cys Gly Leu Cys Glu Arg Ser Phe Val Glu Lys Ser Ala
    1               5                   10                  15

Leu Ser Arg His Gln Arg Val His Lys Asn
                    20                  25
```

(2) INFORMATION FOR SEQ ID NO:56:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:56:

```
    Arg Tyr Ser Cys Ser Glu Cys Gly Lys Cys Phe Thr His Arg Ser Val
    1               5                   10                  15

Phe Leu Lys His Trp Arg Met His Thr Gly
```

20                  25

(2) INFORMATION FOR SEQ ID NO:57:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:57:

Pro Tyr Thr Cys Lys Glu Cys Gly Lys Ser Phe Ser Gln Ser Ser Ala
    1               5                   10                  15

Leu Val Lys His Val Arg Ile His Thr Gly
                    20                  25

(2) INFORMATION FOR SEQ ID NO:58:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:58:

Pro Tyr Ala Cys Ser Thr Cys Gly Lys Ser Phe Ile Gln Lys Ser Asp
    1               5                   10                  15

Leu Ala Lys His Gln Arg Ile His Thr Gly
                    20                  25

(2) INFORMATION FOR SEQ ID NO:59:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:59:

Pro Tyr Thr Cys Thr Val Cys Gly Lys Lys Phe Ile Asp Arg Ser Ser
    1               5                   10                  15

Val Val Lys His Ser Arg Thr His Thr Gly
                    20                  25

(2) INFORMATION FOR SEQ ID NO:60:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:60:

Pro Tyr Lys Cys Asn Glu Cys Thr Lys Gly Phe Val Gln Lys Ser Asp
    1               5                   10                  15

Leu Val Lys His Met Arg Thr His Thr Gly
                    20                  25

(2) INFORMATION FOR SEQ ID NO:61:

(i) SEQUENCE CHARACTERISTICS:
    (A) LENGTH: 26 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:61:

Pro Tyr Gly Cys Asn Cys Cys Asp Arg Ser Phe Ser Thr His Ser Ala
1               5                   10                  15

Ser Val Arg His Gln Arg Met Cys Asn Thr
            20                  25

(2) INFORMATION FOR SEQ ID NO:62:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:62:

Asp Leu His Cys Arg Arg Cys Arg Thr Gln Phe Ser Arg Arg Ser Lys
1               5                   10                  15

Leu His Ile His Gln Lys Leu Arg Cys Gly Gln
            20                  25

(2) INFORMATION FOR SEQ ID NO:63:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:63:

Thr Phe Glu Cys Leu Phe Pro Gly Cys Thr Lys Thr Phe Lys Arg Arg
1               5                   10                  15

Tyr Asn Ile Arg Ser His Ile Gln Thr His Leu Glu
            20                  25

(2) INFORMATION FOR SEQ ID NO:64:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:64:

Pro Tyr Ser Cys Asp His Pro Gly Cys Asp Lys Ala Phe Val Arg Asn
1               5                   10                  15

His Asp Leu Ile Arg His Lys Lys Ser His Gln Glu
            20                  25

(2) INFORMATION FOR SEQ ID NO:65:

(i) SEQUENCE CHARACTERISTICS:
        (A) LENGTH: 26 amino acids
        (B) TYPE: amino acid (C) STRANDEDNESS:
        (D) TOPOLOGY: linear (ii) MOLECULE TYPE: peptide (xi) SEQUENCE DESCRIPTION: SEQ ID NO:65:

Tyr Ala Cys Pro Cys Gly Lys Lys Phe Asn Arg Glu Asp Ala Leu Val
    1               5                   10                  15

Val His Arg Ser Arg Met Ile Cys Ser Gly
                20                  25

(2) INFORMATION FOR SEQ ID NO:66:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:66:

Arg Tyr Ile Cys Ser Phe Ala Asp Cys Gly Ala Ala Tyr Asn Lys Asn
    1               5                   10                  15

Trp Lys Leu Gln Ala His Leu Cys Lys His Thr Gly
                20                  25

(2) INFORMATION FOR SEQ ID NO:67:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:67:

Pro Phe Pro Cys Lys Glu Glu Cys Glu Lys Gly Phe Thr Ser Leu
    1               5                   10                  15

His His Thr Leu Arg His Ser Leu Thr His Thr Gly
                20                  25

(2) INFORMATION FOR SEQ ID NO:68:

(i) SEQUENCE CHARACTERISTICS:
        (A) LENGTH: 29 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:68:

Asn Phe Thr Cys Asp Ser Asp Gly Cys Asp Leu Arg Phe Thr Thr Lys
    1               5                   10                  15

Ala Asn Met Lys Lys His Phe Asn Arg Phe His Asn Ile
                20                  25

(2) INFORMATION FOR SEQ ID NO:69:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:69:

Val Tyr Val Cys His Phe Glu Asn Cys Gly Lys Ala Phe Lys His
1               5                   10                  15

Asn Gln Leu Lys Val His Gln Phe Ser His Thr Gln
                20                  25

(2) INFORMATION FOR SEQ ID NO:70:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:70:

Pro Tyr Glu Cys Pro His Glu Gly Cys Asp Lys Arg Phe Ser Leu Pro
1               5                   10                  15

Ser Arg Leu Lys Arg His Glu Lys Val His Ala Gly
                20                  25

(2) INFORMATION FOR SEQ ID NO:71:

(i) SEQUENCE CHARACTERISTICS:
        (A) LENGTH: 29 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:71:

Tyr Pro Cys Lys Lys Asp Asp Ser Cys Ser Phe Val Gly Lys Thr Trp
1               5                   10                  15

Thr Leu Tyr Leu Lys His Val Ala Glu Cys His Gln Asp
                20                  25

(2) INFORMATION FOR SEQ ID NO:72:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:72:

Ala Val Cys Asp Val Cys Asn Arg Lys Phe Arg His Lys Asp Tyr Leu
1               5                   10                  15

Arg Asp His Gln Lys Thr His Glu Lys
                20                  25

(2) INFORMATION FOR SEQ ID NO:73:

(i) SEQUENCE CHARACTERISTICS:
        (A) LENGTH: 29 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:73:

Val Tyr Leu Cys Pro Arg Asp Gly Cys Asp Arg Ser Tyr Thr Thr Ala

```
                1               5                   10                  15
        Phe Asn Leu Arg Ser His Ile Gln Ser Phe His Glu Glu
                        20                  25
```

(2) INFORMATION FOR SEQ ID NO:74:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:74:

```
        Pro Phe Val Cys Glu His Ala Gly Cys Gly Lys Cys Phe Ala Met Lys
        1               5                   10                  15
        Lys Ser Leu Glu Arg His Ser Val Val His Asp Pro
                        20                  25
```

(2) INFORMATION FOR SEQ ID NO:75:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:75:

```
        Ser Phe Val Cys Glu Val Cys Thr Arg Ala Phe Ala Arg Gln Glu His
        1               5                   10                  15
        Leu Lys Arg His Tyr Arg Ser His Thr Asn
                        20                  25
```

(2) INFORMATION FOR SEQ ID NO:76:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:76:

```
        Pro Tyr Pro Cys Gly Leu Cys Asn Arg Cys Phe Thr Arg Arg Asp Leu
        1               5                   10                  15
        Leu Ile Arg His Ala Gln Lys Ile His Ser Gly
                        20                  25
```

(2) INFORMATION FOR SEQ ID NO:77:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:77:

```
        Thr Tyr Arg Cys Ser Glu Cys Gln Arg Glu Phe Glu Leu Leu Ala Gly
        1               5                   10                  15
        Leu Lys Lys His Leu Lys Thr His Arg Thr
                        20                  25
```

(2) INFORMATION FOR SEQ ID NO:78:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:78:

Lys Tyr Gln Cys Asp Ile Cys Gly Gln Lys Phe Val Gln Lys Ile Asn
    1               5                   10                  15

Leu Thr His His Ala Arg Ile His Ser Ser
                20                  25

(2) INFORMATION FOR SEQ ID NO:79:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:79:

Pro Tyr Glu Cys Pro Glu Cys Gln Lys Arg Phe Gln Glu Arg Ser His
    1               5                   10                  15

Leu Gln Arg His Gln Lys Tyr His Ala Gln
                20                  25

(2) INFORMATION FOR SEQ ID NO:80:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:80:

Ser Tyr Arg Cys Glu Lys Cys Gly Lys Met Tyr Lys Thr Glu Arg Cys
    1               5                   10                  15

Leu Lys Val His Asn Leu Val His Leu Glu
                20                  25

(2) INFORMATION FOR SEQ ID NO:81:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:81:

Pro Phe Ala Cys Thr Val Cys Asp Lys Ser Phe Ile Ser Asn Ser Lys
    1               5                   10                  15

Leu Lys Gln His Ser Asn Ile His Thr Gly
                20                  25

(2) INFORMATION FOR SEQ ID NO:82:

```
    (i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:82:

Pro Phe Lys Cys Asn Tyr Cys Pro Arg Asp Phe Thr Asn Phe Pro Asn
  1               5                  10                  15

Trp Leu Lys His Thr Arg Arg Arg His Lys Val
                  20                  25

(2) INFORMATION FOR SEQ ID NO:83:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:83:

Pro Phe Val Cys Asn Tyr Cys Asp Lys Thr Phe Ser Phe Lys Ser Leu
  1               5                  10                  15

Leu Val Ser His Lys Arg Ile His Thr Gly
                  20                  25

(2) INFORMATION FOR SEQ ID NO:84:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:84:

Pro Tyr Glu Cys Asp Val Cys Gln Lys Thr Phe Ser His Lys Ala Asn
  1               5                  10                  15

Leu Ile Lys His Gln Arg Ile His Thr Gly
                  20                  25

(2) INFORMATION FOR SEQ ID NO:85:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:85:

Pro Phe Glu Cys Pro Glu Cys Gly Lys Ala Phe Thr His Gln Ser Asn
  1               5                  10                  15

Leu Ile Val His Gln Arg Ala His Met Glu
                  20                  25

(2) INFORMATION FOR SEQ ID NO:86:

(i) SEQUENCE CHARACTERISTICS:
        (A) LENGTH: 26 amino acids
        (B) TYPE: amino acid
        (C) STRANDEDNESS:
```

(D) TOPOLOGY: linear (ii) MOLECULE TYPE: peptide (xi) SEQUENCE DESCRIPTION: SEQ ID NO:86:

Pro Tyr Gly Cys Ser Glu Cys Gly Lys Ala Phe Thr His Gln Ser Asn
        1               5                   10                  15

Leu Ile Val His Gln Arg Ile His Thr Gly
                    20                  25

(2) INFORMATION FOR SEQ ID NO:87:

(i) SEQUENCE CHARACTERISTICS:
                (A) LENGTH: 26 amino acids
                (B) TYPE: amino acid
                (C) STRANDEDNESS:
                (D) TOPOLOGY: linear (ii) MOLECULE TYPE: peptide (xi) SEQUENCE DESCRIPTION: SEQ ID NO:87:

Pro Tyr Glu Cys Asn Glu Cys Ala Lys Thr Arg Arg Lys Lys Ser Asn
        1               5                   10                  15

Leu Ile Ile His Gln Lys Ile His Thr Gly
                    20                  25

(2) INFORMATION FOR SEQ ID NO:88:

(i) SEQUENCE CHARACTERISTICS:
                (A) LENGTH: 26 amino acids
                (B) TYPE: amino acid
                (C) STRANDEDNESS:
                (D) TOPOLOGY: linear (ii) MOLECULE TYPE: peptide (xi) SEQUENCE DESCRIPTION: SEQ ID NO:88:

Arg Tyr Glu Cys Asn Glu Cys Gly Lys Ser Phe Ile Gln Asn Ser Gln
        1               5                   10                  15

Leu Ile Ile His Arg Arg Thr His Thr Gly
                    20                  25

(2) INFORMATION FOR SEQ ID NO:89:

(i) SEQUENCE CHARACTERISTICS:
                (A) LENGTH: 26 amino acids
                (B) TYPE: amino acid
                (C) STRANDEDNESS:
                (D) TOPOLOGY: linear (ii) MOLECULE TYPE: peptide (xi) SEQUENCE DESCRIPTION: SEQ ID NO:89:

Pro Tyr Glu Cys Thr Glu Cys Gly Lys Thr Phe Ser Gln Arg Ser Thr
        1               5                   10                  15

Leu Arg Leu His Leu Arg Ile His Thr Gly
                    20                  25

(2) INFORMATION FOR SEQ ID NO:90:

(i) SEQUENCE CHARACTERISTICS:
                (A) LENGTH: 26 amino acids
                (B) TYPE: amino acid
                (C) STRANDEDNESS:
                (D) TOPOLOGY: linear (ii) MOLECULE TYPE: peptide (xi) SEQUENCE DESCRIPTION: SEQ ID NO:90:

Val Tyr Gly Cys Asp Glu Cys Gly Lys Thr Phe Arg Gln Ser Ser Ile
1               5                   10                  15

Leu Leu Lys His Gln Arg Ile His Thr Gly
            20                  25

(2) INFORMATION FOR SEQ ID NO:91:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:91:

Pro Tyr Thr Cys Asn Val Cys Asp Lys His Phe Ile Glu Arg Ser Ser
1               5                   10                  15

Leu Thr Val His Gln Arg Thr His Thr Gly
            20                  25

(2) INFORMATION FOR SEQ ID NO:92:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:92:

Pro Tyr Lys Cys His Glu Cys Gly Lys Ala Phe Ser Gln Ser Met Asn
1               5                   10                  15

Leu Thr Val His Gln Arg Thr His Thr Gly
            20                  25

(2) INFORMATION FOR SEQ ID NO:93:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:93:

Pro Tyr Gln Cys Lys Glu Cys Gly Lys Ala Phe Arg Lys Asn Ser Ser
1               5                   10                  15

Leu Ile Gln His Glu Arg Ile His Thr Gly
            20                  25

(2) INFORMATION FOR SEQ ID NO:94:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:94:

Pro Tyr Lys Cys His Asp Cys Glu Lys Ala Phe Ser Lys Asn Ser Ser
1               5                   10                  15

```
       Leu Thr Gln His Arg Arg Ile His Thr Gly
                    20                  25

(2) INFORMATION FOR SEQ ID NO:95:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:95:

Pro Tyr Glu Cys Met Ile Cys Gly Lys His Phe Thr Gly Arg Ser Ser
       1               5                   10                  15

Leu Thr Val His Gln Val Ile His Thr Gly
                   20                  25

(2) INFORMATION FOR SEQ ID NO:96:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:96:

Pro Tyr Glu Cys Thr Glu Cys Gly Lys Ala Phe Ser Gln Ser Ala Tyr
       1               5                   10                  15

Leu Ile Glu His Arg Arg Ile His Thr Gly
                   20                  25

(2) INFORMATION FOR SEQ ID NO:97:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:97:

Pro Tyr Glu Cys Asp Gln Cys Gly Lys Ala Phe Ile Lys Asn Ser Ser
       1               5                   10                  15

Leu Ile Val His Gln Arg Ile His Thr Gly
                   20                  25

(2) INFORMATION FOR SEQ ID NO:98:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:98:

Pro Tyr Gln Cys Asn Glu Cys Gly Lys Pro Phe Ser Arg Ser Thr Asn
       1               5                   10                  15

Leu Thr Arg His Gln Arg Thr His Thr
                   20                  25
```

(2) INFORMATION FOR SEQ ID NO:99:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:99:

```
Asn Tyr Lys Cys Lys Thr Cys Gly Val Val Ala Ile Thr Lys Val Asp
1               5                   10                  15

Phe Trp Ala His Thr Arg Thr His Met Lys
            20                  25
```

(2) INFORMATION FOR SEQ ID NO:100:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:100:

```
Ile Leu Gln Cys Pro Lys Cys Pro Phe Val Thr Glu Arg Lys His His
1               5                   10                  15

Leu Glu Tyr His Ile Arg Lys His Lys Asn
            20                  25
```

(2) INFORMATION FOR SEQ ID NO:101:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:101:

```
Pro Phe Gln Cys Asp Lys Cys Ser Tyr Thr Cys Val Asn Lys Ser Met
1               5                   10                  15

Leu Asn Ser His Arg Lys Ser His Ser Ser
            20                  25
```

(2) INFORMATION FOR SEQ ID NO:102:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:102:

```
Gln Tyr Arg Cys Ala Asp Cys Asp Tyr Ala Thr Lys Tyr Cys His Ser
1               5                   10                  15

Phe Lys Leu His Leu Arg His Tyr Gly His Lys Pro
            20                  25
```

(2) INFORMATION FOR SEQ ID NO:103:

(i) SEQUENCE CHARACTERISTICS:

(A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:103:

Ile Tyr Glu Cys Lys Tyr Cys Asp Ile Phe Phe Lys Asp Ala Val Leu
    1               5                  10                  15

Tyr Thr Ile His Met Gly Tyr His Ser Cys
                20                  25

(2) INFORMATION FOR SEQ ID NO:104:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:104:

Val Phe Lys Cys Asn Met Cys Gly Glu Lys Cys Asp Gly Pro Val Gly
    1               5                  10                  15

Leu Phe Val His Met Ala Arg Asn Ala His Ser
                20                  25

(2) INFORMATION FOR SEQ ID NO:105:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:105:

Pro Thr Lys Cys Thr Glu Cys Asp Ala Thr Tyr Gln Cys Arg Ser Ser
    1               5                  10                  15

Ala Val Thr His Met Val Asn Lys His Gly Phe
                20                  25

(2) INFORMATION FOR SEQ ID NO:106:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:106:

Val Leu His Cys Thr Ile Cys Ala Ser Lys Phe Ala Val Pro Gly Arg
    1               5                  10                  15

Leu Leu His His Leu Arg Thr Ile His Gly Ile
                20                  25

(2) INFORMATION FOR SEQ ID NO:107:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:107:

```
Pro Phe Gln Cys Asp Leu Cys Glu Ala Ser Phe Gly Thr His Ser Ser
1               5                   10                  15

Leu Ser Leu His Lys Lys Leu Lys His Lys Ser
            20                  25
```

(2) INFORMATION FOR SEQ ID NO:108:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:108:

```
Glu Val Gln Cys Gly Val Cys Gln Lys Val Leu Ser Cys Arg Asp Ser
1               5                   10                  15

Leu Ile Arg His Cys Lys Ala Phe His Lys Gly
            20                  25
```

(2) INFORMATION FOR SEQ ID NO:109:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:109:

```
Met Leu Val Cys Pro Thr Cys Gly Arg Gln Cys Ala Ser Lys Thr Gly
1               5                   10                  15

Leu Thr Leu His Gln Lys Lys Met His Gly Met
            20                  25
```

(2) INFORMATION FOR SEQ ID NO:110:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:110:

```
Pro Tyr Ala Cys Pro Val Glu Ser Cys Asp Arg Arg Phe Ser Arg Ser
1               5                   10                  15

Asp Glu Leu Thr Arg His Ile Arg Ile His Thr Gly
            20                  25
```

(2) INFORMATION FOR SEQ ID NO:111:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:111:

```
    Pro Phe Gln Cys Arg Ile Cys Met Arg Asn Phe Ser Arg Ser Asp His
    1               5                   10                  15

Leu Thr Thr His Ile Arg Thr His Thr Gly
                20                  25
```

(2) INFORMATION FOR SEQ ID NO:112:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:112:

```
    Pro Phe Ala Cys Asp Ile Cys Gly Arg Phe Ala Arg Ser Asp Glu Arg
    1               5                   10                  15

Lys Lys Arg His Thr Lys Ile Lys Leu Arg
                20                  25
```

(2) INFORMATION FOR SEQ ID NO:113:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:113:

```
    Val Tyr Pro Cys Met Ile Cys Gly Lys Lys Phe Lys Ser Arg Gly Phe
    1               5                   10                  15

Leu Lys Arg His Met Lys Asn His Pro Glu
                20                  25
```

(2) INFORMATION FOR SEQ ID NO:114:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:114:

```
    Lys Tyr His Cys Thr Asp Cys Asp Tyr Thr Thr Asn Lys Lys Ile Ser
    1               5                   10                  15

Leu His Asn His Leu Glu Ser His Lys Leu
                20                  25
```

(2) INFORMATION FOR SEQ ID NO:115:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:115:

```
    Ala Ile Glu Cys Asp Glu Cys Gly Lys His Phe Ser His Ala Gly Ala
    1               5                   10                  15
```

```
       Leu Phe Thr His Lys Met Val His Lys Glu
                    20                  25
```

(2) INFORMATION FOR SEQ ID NO:116:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:116:

```
       Met His Lys Cys Lys Phe Cys Glu Tyr Glu Thr Ala Glu Gln Gly Leu
       1               5                  10                  15

Leu Asn Arg His Leu Leu Ala Val His Ser Lys
                    20                  25
```

(2) INFORMATION FOR SEQ ID NO:117:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:117:

```
       Pro His Ile Cys Val Glu Cys Gly Lys Gly Phe Arg His Pro Ser Glu
       1               5                  10                  15

Leu Arg Lys His Met Arg Ile His Thr Gly
                    20                  25
```

(2) INFORMATION FOR SEQ ID NO:118:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:118:

```
       Pro Tyr Gln Cys Gln Tyr Cys Glu Tyr Arg Ser Ala Asp Ser Ser Asn
       1               5                  10                  15

Leu Lys Thr His Ile Lys Thr Lys His Ser Lys
                    20                  25
```

(2) INFORMATION FOR SEQ ID NO:119:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:119:

```
       Pro Phe Lys Cys Asp Ile Cys Leu Leu Thr Phe Ser Asp Thr Lys Glu
       1               5                  10                  15

Val Gln Gln His Thr Leu Val His Gln Glu
                    20                  25
```

(2) INFORMATION FOR SEQ ID NO:120:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:120:

```
Thr His Gln Cys Leu His Cys Asp His Lys Ser Ser Asn Ser Ser Asp
1               5                   10                  15

Leu Lys Arg His Val Ile Ser Val His Thr Lys
            20                  25
```

(2) INFORMATION FOR SEQ ID NO:121:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:121:

```
Pro His Asp Cys Glu Met Cys Glu Lys Gly Phe His Arg Pro Ser Glu
1               5                   10                  15

Leu Lys Lys His Val Ala Val His Lys Gly
            20                  25
```

(2) INFORMATION FOR SEQ ID NO:122:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:122:

```
Met His Gln Cys Arg His Cys Asp Phe Lys Ile Ala Asp Pro Phe Val
1               5                   10                  15

Leu Ser Arg His Ile Leu Ser Val His Thr Lys
            20                  25
```

(2) INFORMATION FOR SEQ ID NO:123:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:123:

```
Pro Phe Arg Cys Lys Arg Cys Arg Lys Gly Phe Arg Gln Gln Asn Glu
1               5                   10                  15

Leu Lys Lys His Met Lys Thr His Ser Gly
            20                  25
```

(2) INFORMATION FOR SEQ ID NO:124:

(i) SEQUENCE CHARACTERISTICS:
        (A) LENGTH: 27 amino acids (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:124:

Val Tyr Gln Cys Glu Tyr Cys Glu Tyr Ser Thr Thr Asp Ala Ser Gly
    1               5                  10                  15

Phe Lys Arg His Val Ile Ser Ile His Thr Lys
                20                  25

(2) INFORMATION FOR SEQ ID NO:125:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:125:

Pro His Arg Cys Glu Tyr Cys Lys Lys Gly Phe Arg Arg Pro Ser Glu
    1               5                  10                  15

Lys Asn Gln His Ile Met Arg His His Lys
                20                  25

(2) INFORMATION FOR SEQ ID NO:126:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:126:

Leu Leu Arg Cys Pro Ala Ala Gly Cys Lys Ala Phe Tyr Arg Lys Glu
    1               5                  10                  15

Gly Lys Leu Gln Asp His Met Ala Gly His Ser Glu
                20                  25

(2) INFORMATION FOR SEQ ID NO:127:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:127:

Pro Trp Lys Cys Gly Ile Lys Asp Cys Asp Lys Val Phe Ala Arg Lys
    1               5                  10                  15

Arg Gln Ile Leu Lys His Val Lys Arg His Leu Ala
                20                  25

(2) INFORMATION FOR SEQ ID NO:128:

(i) SEQUENCE CHARACTERISTICS:
        (A) LENGTH: 29 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:128:

```
Lys Leu Ser Cys Pro Thr Ala Gly Cys Lys Met Thr Phe Ser Thr Lys
 1               5                  10                  15
Lys Ser Leu Ser Arg His Lys Leu Tyr Lys His Gly Glu
            20                  25
```

(2) INFORMATION FOR SEQ ID NO:129:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:129:

```
Pro Leu Lys Cys Phe Val Pro Gly Cys Lys Arg Ser Phe Arg Lys Lys
 1               5                  10                  15
Arg Ala Leu Arg Arg His Leu Ser Val His Ser Asn
            20                  25
```

(2) INFORMATION FOR SEQ ID NO:130:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:130:

```
Leu Ser Val Cys Asp Val Pro Gly Cys Ser Trp Lys Ser Ser Ser Val
 1               5                  10                  15
Ala Lys Leu Val Ala His Gln Lys Arg His Arg Gly
            20                  25
```

(2) INFORMATION FOR SEQ ID NO:131:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:131:

```
Tyr Arg Cys Ser Tyr Glu Gly Cys Gln Thr Val Ser Pro Thr Trp Thr
 1               5                  10                  15
Ala Leu Gln Thr His Val Lys Lys His Pro Leu
            20                  25
```

(2) INFORMATION FOR SEQ ID NO:132:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:132:

```
Leu Gln Cys Ala Ala Cys Lys Lys Pro Phe Lys Lys Ala Ser Ala Leu
1               5                   10                  15

Arg Arg His Lys Ala Thr His Ala Lys
            20                  25
```

(2) INFORMATION FOR SEQ ID NO:133:

(i) SEQUENCE CHARACTERISTICS:
        (A) LENGTH: 30 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:133:

```
Gln Leu Pro Cys Pro Arg Gln Asp Cys Asp Lys Thr Phe Ser Ser Val
1               5                   10                  15

Phe Asn Leu Thr His His Val Ala Arg Lys Leu His Leu Cys
            20                  25                  30
```

(2) INFORMATION FOR SEQ ID NO:134:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:134:

```
Thr His Arg Cys Pro His Ser Gly Cys Thr Arg Ser Phe Ala Met Arg
1               5                   10                  15

Glu Ser Leu Leu Arg His Leu Val Val His Asp Pro
            20                  25
```

(2) INFORMATION FOR SEQ ID NO:135:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:135:

```
Tyr Gln Cys Gln Tyr Cys Glu Lys Arg Phe Ala Asp Ser Ser Asn Leu
1               5                   10                  15

Lys Thr His Ile Lys Thr Lys His Ser
            20                  25
```

(2) INFORMATION FOR SEQ ID NO:136:

(i) SEQUENCE CHARACTERISTICS:
        (A) LENGTH: 33 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 4..7
        (D) OTHER INFORMATION: /product= "may encompass 2-4 amino
            acids"

```
            -continued (ix) FEATURE:
         (A) NAME/KEY: Modified-site
         (B) LOCATION: 22..26
         (D) OTHER INFORMATION: /product= "may encompass 3-5 amino
             acids"

(ix) FEATURE:
         (A) NAME/KEY: Modified-site
         (B) LOCATION: 28..33
         (D) OTHER INFORMATION: /product= "may encompass 2-6 amino
             acids"

(ix) FEATURE:
         (A) NAME/KEY: Modified-site
         (B) LOCATION: 9..11
         (D) OTHER INFORMATION: /product= "may encompass 1-3 amino
             acids"

(ix) FEATURE:
         (A) NAME/KEY: Modified-site
         (B) LOCATION: 13..17
         (D) OTHER INFORMATION: /product= "may encompass 1-5 amino
             acids"

(ix) FEATURE:
         (A) NAME/KEY: Modified-site
         (B) LOCATION: 19..20
         (D) OTHER INFORMATION: /product= "may encompass 1-2 amino
             acids"

(xi) SEQUENCE DESCRIPTION: SEQ ID NO:136:

Xaa Xaa Cys Xaa Xaa Xaa Xaa Cys Xaa Xaa Xaa Xaa Xaa Xaa Xaa
    1           5                   10                  15

Xaa Xaa Xaa Xaa His Xaa Xaa Xaa Xaa Xaa His Xaa Xaa Xaa Xaa Xaa
                20                  25                  30

Xaa
```